United States Patent
Lee

(10) Patent No.: US 10,738,279 B2
(45) Date of Patent: Aug. 11, 2020

(54) MODIFIED NK-92 CELLS FOR TREATING CANCER

(71) Applicant: NantKwest, Inc., Culver City, CA (US)

(72) Inventor: Tien Lee, Culver City, CA (US)

(73) Assignee: NantKwest, Inc., Culver City, CA (US)

(*) Notice: Subject to any disclaimer, the term of this patent is extended or adjusted under 35 U.S.C. 154(b) by 0 days.

(21) Appl. No.: 15/531,109

(22) PCT Filed: Jun. 10, 2016

(86) PCT No.: PCT/US2016/036991
§ 371 (c)(1),
(2) Date: May 26, 2017

(87) PCT Pub. No.: WO2016/201304
PCT Pub. Date: Dec. 15, 2016

(65) Prior Publication Data
US 2018/0163176 A1    Jun. 14, 2018

Related U.S. Application Data

(60) Provisional application No. 62/173,701, filed on Jun. 10, 2015, provisional application No. 62/337,044, filed on May 16, 2016.

(51) Int. Cl.
| | |
|---|---|
| *C12N 5/0783* | (2010.01) |
| *C07K 16/28* | (2006.01) |
| *A61K 39/395* | (2006.01) |
| *C07K 14/54* | (2006.01) |
| *A61K 35/17* | (2015.01) |
| *A61K 39/00* | (2006.01) |
| *A61P 35/00* | (2006.01) |

(52) U.S. Cl.
CPC ............ *C12N 5/0646* (2013.01); *A61K 35/17* (2013.01); *A61K 39/00* (2013.01); *A61K 39/001129* (2018.08); *A61K 39/395* (2013.01); *A61P 35/00* (2018.01); *C07K 14/54* (2013.01); *C07K 16/28* (2013.01); *C07K 16/2803* (2013.01); *A61K 2039/505* (2013.01); *A61K 2039/5156* (2013.01); *C07K 2317/622* (2013.01); *C07K 2317/732* (2013.01); *C07K 2317/92* (2013.01); *C07K 2319/03* (2013.01); *C07K 2319/04* (2013.01); *C07K 2319/30* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 7,351,801 B2 * | 4/2008 | Belew | C07K 14/765 530/364 |
| 7,618,817 B2 | 11/2009 | Campbell | |
| 8,034,332 B2 | 10/2011 | Klingemann | |
| 8,313,943 B2 | 11/2012 | Campbell | |
| 8,906,682 B2 | 12/2014 | June et al. | |
| 8,946,385 B2 | 2/2015 | Kawai | |
| 2013/0040386 A1 | 2/2013 | Campbell | |

FOREIGN PATENT DOCUMENTS

| | | |
|---|---|---|
| EP | 2123754 A1 | 11/2009 |
| EP | 2161339 A1 | 3/2010 |
| WO | 2014055668 A1 | 4/2014 |

OTHER PUBLICATIONS

Tassev et al (CGT, 19:84-100, 2012).*
Konstantinidis et al (EH, 33:159-164, 2005).*
Mariuzza et al. (Annu. Rev. Biophys. Biophys. Chem. 1987; 16: 139-159).*
Gussow et al. (Methods in Enzymology. 1991; 203: 99-121).*
Winkler et al (J. Imm., 265:4505-4514, 2000).*
Hermanson, et al., "Utilizing chimeric antigen receptors to direct natural killer cell activity," Frontiers in Immunology, Apr. 28, 2015, vol. 6, Article 195, pp. 1-6.
Clemenceau, et al., "The human natural killer cytotoxic cell line NK-92, once armed with a murine CD16 receptor, represents a convenient cellular tool for the screening of mouse mAbs according to their ADCC potential," Mabs, 2013, vol. 5, No. 4, pp. 587-594.
PCT/US2016/036991 "International Search Report and Written Opinion," dated Nov. 18, 2016, 19 pages.
Glienke, et al., "Advantages and applications of CAR-expressing natural killer cells," Frontiers in Pharmacology, Feb. 2015, vol. 6.
Boissel et al., "Retargeting NK-92 cells by means of CD19- and CD20-specific chimeric antigen receptors compares favorably with antibody-dependent cellular cytotoxicity," OncoImmunology, Oct. 2013, vol. 2, Issue 10, e26527, 8 pages.
Extended European Search Report for European Patent Application No. 16808427.5 dated Mar. 6, 2019, pp. 8.

* cited by examiner

*Primary Examiner* — Brad Duffy
(74) *Attorney, Agent, or Firm* — Martin Fessenmaier; Umberg Zipser, LLP

(57) ABSTRACT

Provided herein are NK-92 cells expressing at least one CAR and at least one Fc receptor. Also provided are methods of treatment of a patient having or suspected of having a disease that is treatable with NK-92 cells, such as cancer, comprising administering to the patient NK-92-Fc-CAR.

20 Claims, 2 Drawing Sheets
Specification includes a Sequence Listing.

MODIFIED NK-92 CELLS FOR TREATING CANCER

CROSS-REFERENCE TO RELATED APPLICATIONS

This application is a 35 USC § 371 national stage entry of International Application No. PCT/US2016/036991 filed Jun. 10, 2016, which claims the benefit of priority to U.S. Provisional Application No. 62/173,701 filed Jun. 10, 2015 and U.S. Provisional Application No. 62/337,044 filed May 16, 2016, each of which is incorporated by reference herein in its entirety.

REFERENCE TO SUBMISSION OF A SEQUENCE LISTING AS A TEXT FILE

The Sequence Listing written in file SEQ_LIST-ING_099083-1050738.txt created on Nov. 8, 2017, 32,349 bytes, machine format IBM-PC, MS-Windows operating system, is hereby incorporated by reference in its entirety for all purposes.

BACKGROUND

Natural killer (NK) cells are cytotoxic lymphocytes that constitute a major component of the innate immune system. NK cells, generally representing about 10-15% of circulating lymphocytes, bind and kill targeted cells, including virus-infected cells and many malignant cells, non-specifically with regard to antigen and without prior immune sensitization. Herberman et al., Science 214:24 (1981). Killing of targeted cells occurs by inducing cell lysis. NK cells used for this purpose are isolated from the peripheral blood lymphocyte ("PBL") fraction of blood from the subject, expanded in cell culture in order to obtain sufficient numbers of cells, and then re-infused into the subject. NK cells have been shown to be somewhat effective in both ex vivo therapy and in vivo treatment. However, such therapy is complicated by the fact that not all NK cells are cytolytic and the therapy is specific to the treated patient.

With cancer, phenotypic changes distinguishing a tumor cell from normal cells derived from the same tissue are often associated with one or more changes in the expression of specific gene products, including the loss of normal cell surface components or the gain of others (i.e., antigens not detectable in corresponding normal, non-cancerous tissue). The antigens which are expressed in neoplastic or tumor cells, but not in normal cells, or which are expressed in neoplastic cells at levels substantially above those found in normal cells, have been termed "tumor-specific antigens" or "tumor-associated antigens." Such tumor-specific antigens may serve as markers for tumor phenotype. Tumor-specific antigens can be assigned to three main groups: cancer/testis-specific antigen (e.g. MAGE, BAGE, GAGE, PRAME and NY-ESO-1), melanocyte differentiation antigens (e.g. tyrosinase, Melan-A/MART, gp100, TRP-1 and TRP-2) and mutated or aberrantly expressed antigens (e.g. MUM-1, CDK4, beta-catenin, gp100-in4, p15 and N-acetylglucosaminyltransferase V).

Tumor-specific antigens have been used as targets for cancer immunotherapies. One such therapy utilizes chimeric antigen receptors (CARs) expressed on the surface of immune cells, including T cells and NK cells, to improve cytotoxicity against cancer cells. CARs comprise a single-chain variable fragment (scFv) linked to at least one intracellular signaling domain. The scFv recognizes and binds an antigen on the target cell (e.g., a cancer cell) and triggers effector cell activation.

In addition, anticancer treatment with monoclonal antibodies (mAbs) has significantly improved the clinical outcome in patients with cancer, especially when combined with chemotherapy. However, cancer cells are known to escape from immune-mediated rejection despite the presentation of antigens by the malignant cells and the presence of immune cells. One mechanism by which cancer cells escape immune eradication is by preventing detection. For example, tumor escape mechanisms include impaired or reduced antigen presentation (e.g., mutation or downregulation of tumor antigens) which reduces the efficacy of single target therapies such as CAR-expressing immune cells and mAbs. As such, improved therapeutics and methods of treating cancer cells are still needed.

BRIEF SUMMARY

Provided herein are genetically modified NK-92 cells or cell lines engineered to express multiple transgenes. For example, an NK-92 cell is modified to concurrently express at least one Fc receptor and at least one chimeric antigen receptor (CAR), such that the at least one Fc receptor and the at least one CAR are displayed on the cell surface of the NK-92 cell.

Thus, the present disclosure provides for an NK-92 cell line wherein cells of the NK-92 cell line are modified to express at least one Fc receptor and at least one chimeric antigen receptor (CAR) such that the Fc receptor and CAR are displayed on the cell surface of the NK-92 cells.

The foregoing general description and the following detailed description are exemplary and explanatory and are intended to provide further explanation of the disclosure. Other objects, advantages and novel features will be readily apparent to those skilled in the art.

BRIEF DESCRIPTION OF THE DRAWINGS

The objects, features and advantages will be more readily appreciated upon reference to the following disclosure when considered in conjunction with the accompanying drawings.

FIG. 1A shows killing of target cell lines by non-electroporated parental NK-92 cells. FIG. 1B shows killing of target cell lines by parental NK-92 cells expressing CD19-CAR. FIG. 1C shows killing of target cell lines by CD16(158V)-ERIL2 NK-92 cells expressing CD19-CAR.

DETAILED DESCRIPTION

Figure 1A:
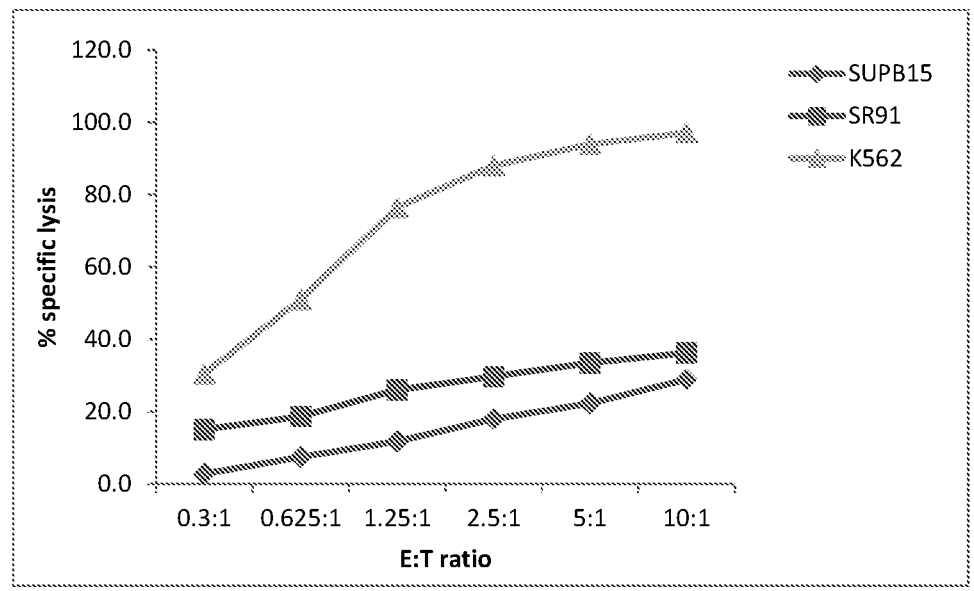
FIGS. 1A, 1B, and 1C are graphs showing in vitro cytotoxicity assays.

Provided herein are NK-92 cells modified to express at least one Fc receptor and at least one chimeric antigen receptor (CAR), such that the at least one Fc receptor and the at least one CAR are displayed on the cell surface of the NK-92 cell. Optionally, the Fc receptor comprises FcγRIII-A (CD16). Optionally, the NK-92 cells are genetically modified to express an Fc receptor encoding a polypeptide having at least 90% sequence identity with SEQ ID NO: 1 (FcγRIII-A or CD16 having a phenylalanine at position 158 (F-158); or at least 90% identity to SEQ ID NO: 2 (CD16 having a valine at position 158 (F158V), higher affinity form). In typical embodiments, the CD16 polypeptide has a valine at position 158. Optionally, the NK-92 cells are genetically modified to express a CAR encoding a polypeptide having at least 90% sequence identity with SEQ ID NO: 8 (CD19), SEQ ID NO: 9 (CD19), SEQ ID NO: 10 (CD33), SEQ ID NO: 11 (CD33), SEQ ID NO: 12 (CSPG-4), or SEQ ID NO: 13 (CSPG-4). Optionally, the CAR targets a tumor-associated antigen, for example, CD19, CD20, NKG2D ligands, CS1, GD2, CD138, EpCAM, HER-2, EBNA3C, GPA7, CD244, CA-125, MUC-1, ETA, MAGE, CEA, CD52, CD30, MUCSAC, c-Met, EGFR, FAB, WT-1, PSMA, NY-ESO1, and CD33. In some embodiments, the NK-92 cells of the cell line undergo less than 10 population doublings.

Optionally, the NK-92 cells further express a cytokine, for example, interleukin-2 or a variant thereof. In some embodiments, the NK-92 cells are modified to express a polypeptide having a sequence of SEQ ID NO: 6 or SEQ ID NO: 7. In further embodiments, the cytokine is targeted to the endoplasmic reticulum. Optionally, the NK-92 cells of the cell line are cultured in media containing less than 10 U/ml of IL-2.

The present disclosure provides for a composition comprising any of the NK-92 cells described herein. Optionally, the present disclosure provides for a composition of any of the NK-92 cells of the above embodiments and at least one antibody, for example, alemtuzumab, rituxumab, trastuzumab, ibritumomab, gemtuzumab, brentuximab, adotranstuzumab, blinatunomab, daratumumab or elotuzumab. In some embodiments, the monoclonal antibody is a naked monoclonal antibody, a conjugated monoclonal antibody or a bispecific monoclonal antibody.

The present disclosure provides methods of treating cancer in a patient in need thereof, comprising administering to the patient an effective amount of cells of any of the above embodiments. In some embodiments, the cells are administered to the patient by a route selected from the group consisting of intravenous, intraperitoneal, and subcutaneous. In some embodiments, about $1\times10^8$ to about $1\times10^{11}$ cells per $m^2$ of body surface area of the patient are administered to the patient. Optionally, methods of the present disclosure further provide for administering to the patient an effective amount of at least one monoclonal antibody, for example, alemtuzumab, rituxumab, trastuzumab, ibritumomab, gemtuzumab, brentuximab, adotranstuzumab, blinatunomab, daratumumab or elotuzumab. In some embodiments, the monoclonal antibody is a naked monoclonal antibody, a conjugated monoclonal antibody or a bispecific monoclonal antibody. In some embodiments, the monoclonal antibody is administered to the patient by a route selected from the group consisting of intravenous, intraperitoneal, and subcutaneous. In one embodiment, the monoclonal antibody and the cells are administering concurrently. In some embodiments, the monoclonal antibody and the cells are admixed together prior to administering to the patient. In other embodiments, the monoclonal antibody and the cells are administered sequentially. In other embodiments, the subject is administered the monoclonal antibody and subsequently administered the modified NK-92 cells, e.g., within 24 hours; or within 24 to 72 hours, after administration of the monoclonal antibody.

In one embodiment, the cancer is, for example, a leukemia (e.g., chronic B-cell leukemia, acute lymphoblastic leukemia (ALL), chronic lymphocytic leukemia (CLL)), a lymphoma (e.g., non-Hodgkin's lymphoma (NHL)), polycythemia vera, multiple myeloma, Waldenstrom's macroglobulinemia, heavy chain disease, a sarcoma or a carcinoma.

The present disclosure provides kits to be used in any of the above methods of treating cancer, wherein the kit comprises at least one of: (a) an amount of NK-92 cells that are modified to express at least one Fc receptor on a cell surface and at least one a chimeric antigen receptor (CAR) on the cell surface and (b) instructions describing at least one method of the present disclosure. In some embodiments, the kits further comprise at least one monoclonal antibody.

After reading this description, it will become apparent to one skilled in the art how to implement various alternative embodiments and alternative applications. However, not all embodiments are described herein. It will be understood that the embodiments presented here are presented by way of an example only, and not limitation. As such, this detailed description of various alternative embodiments should not be construed to limit the scope or breadth of the disclosure as set forth herein. It is to be understood that the aspects described below are not limited to specific compositions, methods of preparing such compositions, or uses thereof as such may, of course, vary.

Terminology

Unless defined otherwise, all technical and scientific terms used herein have the same meaning as commonly understood by one of ordinary skill in the art.

In this specification and in the claims that follow, reference will be made to a number of terms that shall be defined to have the following meanings:

The terminology used herein is for the purpose of describing particular embodiments only and is not intended to be limiting. As used herein, the singular forms "a," "an" and "the" are intended to include the plural forms as well, unless the context clearly indicates otherwise. Thus, for example, reference to "a natural killer cell" includes a plurality of natural killer cells.

All numerical designations, e.g., pH, temperature, time, concentration, amounts, and molecular weight, including ranges, are approximations which are varied (+) or (-) by increments of 0.1 or 1.0, where appropriate. It is to be understood, although not always explicitly stated, that all numerical designations may be preceded by the term "about."

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

It is also to be understood, although not always explicitly stated, that the reagents described herein are merely exemplary and that equivalents of such are known in the art.

"Optional" or "optionally" means that the subsequently described event or circumstance can or cannot occur, and that the description includes instances where the event or circumstance occurs and instances where it does not.

The term "comprising" is intended to mean that the compositions and methods include the recited elements, but not excluding others. "Consisting essentially of," when used to define compositions and methods, shall mean excluding other elements of any essential significance to the combination. For example, a composition consisting essentially of the elements as defined herein would not exclude other elements that do not materially affect the basic and novel characteristic(s) of the claims. "Consisting of" shall mean excluding more than trace amount of other ingredients and substantial method steps. Embodiments defined by each of these transition terms are within the scope of the disclosure.

As used herein, "concurrent" or "concurrently" refers to the administration of at least two agents (e.g. NK-92-Fc-CAR cells and a monoclonal antibody) at the same time or at approximately the same time As used herein, the term "effective amount" refers to a quantity of a composition sufficient to achieve a desired therapeutic effect, e.g., an amount which results in the amelioration of the cancer cells or one or more symptoms associated with cancer. In the context of therapeutic applications, the amount of NK-92 cells or antibody administered to the subject will depend on the type and progression of the cancer and on the characteristics of the individual, such as general health, age, sex, body weight and tolerance to drugs. It will also depend on the degree, severity and type of disease. The skilled artisan will be able to determine appropriate dosages depending on these and other factors. NK-92 cells can also be administered in combination with one or more additional therapeutic compounds (e.g., antibodies).

As used herein, the term "expression" refers to the process by which polynucleotides are transcribed into mRNA and/or the process by which the transcribed mRNA is subsequently translated into peptides, polypeptides, or proteins. If the polynucleotide is derived from genomic DNA, expression may include splicing of the mRNA in a eukaryotic cell. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of NK-92 cells.

As used herein, "immunotherapy" refers to the use of NK-92 cells, modified or unmodified, naturally occurring or modified NK cell or T-cell, whether alone or in combination, and which are capable of inducing cytotoxicity when contacting a target cell.

As used herein, "natural killer (NK) cells" are cells of the immune system that kill target cells in the absence of a specific antigenic stimulus, and without restriction according to major histocompatibility complex (MHC) class. Target cells may be cancer or tumor cells. NK cells are characterized by the presence of CD56 and the absence of CD3 surface markers.

The term "endogenous NK cells" is used to refer to NK cells derived from a donor (or the patient), as distinguished from the NK-92 cell line. Endogenous NK cells are generally heterogeneous populations of cells within which NK cells have been enriched. Endogenous NK cells may be intended for autologous or allogeneic treatment of a patient.

"NK-92 cells" refer to the immortal NK cell line, NK-92, which was originally obtained from a patient having non-Hodgkin's lymphoma. The term "NK-92" is intended to refer to the original NK-92 cell lines as well as NK-92 cell lines that have been modified (e.g., by introduction of exogenous genes). NK-92 cells and exemplary and non-limiting modifications thereof are described in U.S. Pat. Nos. 7,618,817; 8,034,332; and 8,313,943 all of which are incorporated herein by reference in their entireties.

A "modified NK-92 cell" refers to an NK-92 cell that further comprises a vector that encodes for a transgene, including an Fc receptor, CAR, IL-2, and/or a suicide gene. In a preferred embodiment, the modified NK-92 cell expresses at least one transgenic protein.

As used herein, "non-irradiated NK-92 cells" are NK-92 cells that have not been irradiated. Irradiation renders the cells incapable of growth and proliferation. It is envisioned that the NK-92 cells will be irradiated at the treatment facility or some other point prior to treatment of a patient, since the time between irradiation and infusion should be no longer than four hours in order to preserve optimal activity. Alternatively, NK-92 cells may be inactivated by another mechanism.

As used herein, "inactivation" of the NK-92 cells renders them incapable of growth. Inactivation may also relate to the death of the NK-92 cells. It is envisioned that the NK-92 cells may be inactivated after they have effectively purged an ex vivo sample of cells related to a pathology in a therapeutic application, or after they have resided within the body of a mammal a sufficient period of time to effectively kill many or all target cells residing within the body. Inactivation may be induced, by way of non-limiting example, by administering an inactivating agent to which the NK-92 cells are sensitive.

As used herein, the terms "cytotoxic" and "cytolytic," when used to describe the activity of effector cells such as NK cells, are intended to be synonymous. In general, cytotoxic activity relates to killing of target cells by any of a variety of biological, biochemical, or biophysical mechanisms. Cytolysis refers more specifically to activity in which the effector lyses the plasma membrane of the target cell, thereby destroying its physical integrity. This results in the killing of the target cell. Without wishing to be bound by theory, it is believed that the cytotoxic effect of NK cells is due to cytolysis.

The term "kill" with respect to a cell/cell population is directed to include any type of manipulation that will lead to the death of that cell/cell population.

The term "Fc receptor" refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified based on the type of antibody they recognize. For example, Fc-gamma receptors (FcγR) bind to the IgG class of antibodies. FcγRIII-A (also called CD16) is a low affinity Fc receptor bind to IgG antibodies and activate ADCC. FcγRIII-A are typically found on NK cells. NK-92 cells do not express FcγRIII-A. A representative polynucleotide sequence encoding a native form of CD16 is shown in SEQ ID NO: 5.

The term "chimeric antigen receptor" (CAR), as used herein, refers to an extracellular antigen-binding domain that is fused to an intracellular signaling domain. CARs can be expressed in T cells or NK cells to increase cytotoxicity. In general, the extracellular antigen-binding domain is a scFv that is specific for an antigen found on a cell of interest. A CAR-expressing NK-92 cell is targeted to cells expressing certain antigens on the cell surface, based on the specificity of the scFv domain. The scFv domain can be engineered to recognize any antigen, including tumor-specific antigens.

The term "tumor-specific antigen" as used herein refers to antigens that are present on a cancer or neoplastic cell but not detectable on a normal cell derived from the same tissue or lineage as the cancer cell. Tumor-specific antigens, as used herein, also refers to tumor-associated antigens, that is, antigens that are expressed at a higher level on a cancer cell as compared to a normal cell derived from the same tissue or lineage as the cancer cell.

The terms "polynucleotide", "nucleic acid" and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine when the polynucleotide is RNA. Thus, the term "polynucleotide sequence" is the alphabetical representation of a polynucleotide molecule.

As used herein, "percent identity" refers to sequence identity between two peptides or between two nucleic acid molecules. Percent identity can be determined by comparing a position in each sequence which may be aligned for purposes of comparison. When a position in the compared sequence is occupied by the same base or amino acid, then the molecules are identical at that position. As used herein, the phrase "homologous" or "variant" nucleotide sequence," or "homologous" or "variant" amino acid sequence refers to sequences characterized by identity, at the nucleotide level or amino acid level, of at least a specified percentage. Homologous nucleotide sequences include those sequences coding for naturally occurring allelic variants and mutations of the nucleotide sequences set forth herein. Homologous nucleotide sequences include nucleotide sequences encoding for a protein of a mammalian species other than humans. Homologous amino acid sequences include those amino acid sequences which contain conservative amino acid substitutions and which polypeptides have the same binding and/or activity. In some embodiments, a homologous nucleotide or amino acid sequence has at least 60% or greater, for example at least 70%, or at least 80%, at least 85% or greater, with a comparator sequence. In some embodiments, a homologous nucleotide or amino acid sequence has at least 90%, 91%, 92%, 93%, 94%, 95%, 96%, 97%, 98% or 99% identity with a comparator sequence. In some embodiments, a homologous amino acid sequence has no more than 15, nor more than 10, nor more than 5 or no more than 3 conservative amino acid substitutions. Percent identity can be determined by, for example, the Gap program (Wisconsin Sequence Analysis Package, Version 8 for UNIX, Genetics Computer Group, University Research Park, Madison Wis.), using default settings, which uses the algorithm of Smith and Waterman (Adv. Appl. Math., 1981, 2, 482-489).

The term "expression" refers to the production of a gene product. The term "transient" when referred to expression means a polynucleotide is not incorporated into the genome of the cell.

The term "cytokine" or "cytokines" refers to the general class of biological molecules which effect cells of the immune system. Exemplary cytokines include, but are not limited to, interferons and interleukins (IL), in particular IL-2, IL-12, IL-15, IL-18 and IL-21. In preferred embodiments, the cytokine is IL-2.

As used herein, the term "vector" refers to a non-chromosomal nucleic acid comprising an intact replicon such that the vector may be replicated when placed within a permissive cell, for example by a process of transformation. A vector may replicate in one cell type, such as bacteria, but have limited ability to replicate in another cell, such as mammalian cells. Vectors may be viral or non-viral. Exemplary non-viral vectors for delivering nucleic acid include naked DNA; DNA complexed with cationic lipids, alone or in combination with cationic polymers; anionic and cationic liposomes; DNA-protein complexes and particles comprising DNA condensed with cationic polymers such as heterogeneous polylysine, defined-length oligopeptides, and polyethylene imine, in some cases contained in liposomes; and the use of ternary complexes comprising a virus and polylysine-DNA.

As used herein, the term "targeted" is intended to include, but is not limited to, directing proteins or polypeptides to appropriate destinations in the cell or outside of it. The targeting is typically achieved through signal peptides or targeting peptides, which are a stretch of amino acid residues in a polypeptide chain. These signal peptides can be located anywhere within a polypeptide sequence, but are often located on the N-terminus. Polypeptides can also be engineered to have a signal peptide on the C-terminus. Signal peptides can direct a polypeptide for extracellular section, location to plasma membrane, golgi, endosomes, endoplasmic reticulum, and other cellular compartments. For example, polypeptides with a particular amino acid sequence on their C-terminus (e.g., KDEL) are retained in the ER lumen or transported back the ER lumen.

The term "suicide gene" is one that allows for the negative selection of the cells. A suicide gene is used as a safety system, allowing the cells expressing the gene to be killed by introduction of a selective agent. This is desirable in case the recombinant gene causes a mutation leading to uncontrolled cell growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene (also see, for example, Yazawa K, Fisher W E, Brunicardi F C: Current progress in suicide gene therapy for cancer. World J. Surg. 2002 July; 26(7):783-9). In one embodiment, the suicide gene is inducible caspase 9 (iCas9) (Di Stasi, (2011) "Inducible apoptosis as a safety switch for adoptive cell therapy." N Engl J Med 365: 1673-1683. See also Morgan, "Live and Let Die: A New Suicide Gene Therapy Moves to the Clinic" *Molecular Therapy* (2012); 20: 11-13).

The TK gene may be a wild-type or mutant TK gene (e.g., tk30, tk75, sr39tk). Cells expressing the TK protein can be killed using ganciclovir.

The terms "patient," "subject," "individual," and the like are used interchangeably herein, and refer to any animal, or cells thereof whether in vitro or in situ, amenable to the methods described herein. In a preferred embodiment, the patient, subject, or individual is a mammal. In a particularly preferred embodiment, the patient, subject or individual is a human.

The term "treating" or "treatment" covers the treatment of a disease or disorder described herein, in a subject, such as a human, and includes: (i) inhibiting a disease or disorder, i.e., arresting its development; (ii) relieving a disease or disorder, i.e., causing regression of the disorder; (iii) slowing progression of the disorder; and/or (iv) inhibiting, relieving, or slowing progression of one or more symptoms of the disease or disorder. The term "administering" or "administration" of a monoclonal antibody or a natural killer cell to a subject includes any route of introducing or delivering the antibody or cells to perform the intended function. Administration can be carried out by any route suitable for the delivery of the cells or monoclonal antibody. Thus, delivery routes can include intravenous, intramuscular, intraperitoneal, or subcutaneous deliver. In some embodiments a monoclonal antibody and/or NK-92 cells are administered directly to the tumor, e.g., by injection into the tumor. Administration includes self-administration and the administration by another.

By effective dose or amount as used herein is meant a dose of an agent or composition containing the agent that produces the desired effect(s) (e.g., treating or preventing a disease). The exact dose and formulation of the nanoparticles will depend on the purpose of the treatment and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington (2005); and Pickar, Dosage Calculations (9th edition) (1999)). For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a standard control. A therapeutically effective dose or amount may ameliorate one or more symptoms of a disease. A therapeutically effective dose or amount may prevent or delay the onset of a disease or one or more symptoms of a disease when the effect for which it is being administered is to treat a person who is at risk of developing the disease.

As used herein, the term "antibody" refers to an immunoglobulin or fragment thereof. The antibody may be of any type (e.g., IgG, IgA, IgM, IgE or IgD). Preferably, the antibody is IgG. An antibody may be non-human (e.g., from mouse, goat, or any other animal), fully human, humanized, or chimeric. An antibody may be polyclonal or monoclonal. Optionally, the antibody is monoclonal.

The term "monoclonal antibody" as used herein, refers to a pure, target-specific antibody produced from a single clone of cells grown in culture and that is capable of proliferating indefinitely. Monoclonal antibodies that may be used include naked antibodies, that attach to and block antigens on cancerous cells. In one embodiment, the naked monoclonal antibody is alemtuzumab, which binds to the CD52 antigen in lymphocytes. Also included in the monoclonal antibodies that may be used are conjugated monoclonal antibodies, such as tagged, labeled or loaded antibodies. Specifically, the antibodies may be tagged or loaded with a drug or a toxin, or radioactively labeled. Examples of such antibodies include, but are not limited to, ibritumomab, which targets the CD20 antigen; brentuximab, which targets the CD30 antigen, and trastuzumab, which targets the HER2 protein. Other monoclonal antibodies that may be used are bispecific monoclonal antibodies, such as blinatunomab, which targets CD19 in lymphoma cells, and CD3 in T cells.

As used herein, the term "antibody fragment" refers to any portion of the antibody that recognizes an epitope. Antibody fragments may be glycosylated. By way of non-limiting example, the antibody fragment may be a Fab fragment, a Fab' fragment, a F(ab')2 fragment, a Fv fragment, an rIgG fragment, a functional antibody fragment, single chain recombinant forms of the foregoing, and the like. F(ab')2, Fab, Fab' and Fv are antigen-binding fragments that can be generated from the variable region of IgG and IgM. They vary in size, valency, and Fc content. The fragments may be generated by any method, including expression of the constituents (e.g., heavy and light chain portions) by a cell or cell line, or multiple cells or cell lines. Preferably, the antibody fragment recognizes the epitope and contains a sufficient portion of an Fc region such that it is capable of binding an Fc receptor.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and Medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

Titles or subtitles may be used in the specification for the convenience of a reader, which are not intended to influence the scope of the present disclosure. Additionally, some terms used in this specification are more specifically defined below.

NK-92 Cells

The NK-92 cell line is a unique cell line that was discovered to proliferate in the presence of interleukin 2 (IL-2). Gong et al., *Leukemia* 8:652-658 (1994). These cells have high cytolytic activity against a variety of cancers. The NK-92 cell line is a homogeneous cancerous NK cell population having broad anti-tumor cytotoxicity with predictable yield after expansion. Phase I clinical trials have confirmed its safety profile. NK-92 was discovered in the blood of a subject suffering from a non-Hodgkins lymphoma and then immortalized ex vivo. NK-92 cells are derived from NK cells, but lack the major inhibitory receptors that are displayed by normal NK cells, while retaining the majority of the activating receptors. NK-92 cells do not, however, attack normal cells nor do they elicit an unacceptable immune rejection response in humans. Characterization of the NK-92 cell line is disclosed in WO 1998/49268 and U.S. Patent Application Publication No. 2002-0068044.

The NK-92 cell line is found to exhibit the CD56$^{bright}$, CD2, CD7, CD11a, CD28, CD45, and CD54 surface markers. It furthermore does not display the CD1, CD3, CD4, CD5, CD8, CD10, CD14, CD16, CD19, CD20, CD23, and CD34 markers. Growth of NK-92 cells in culture is dependent upon the presence of recombinant interleukin 2 (rIL-2), with a dose as low as 1 IU/mL being sufficient to maintain proliferation. IL-7 and IL-12 do not support long-term growth, nor do other cytokines tested, including IL-1α, IL-6, tumor necrosis factor α, interferon α, and interferon γ. NK-92 has high cytotoxicity even at a low effector:target (E:T) ratio of 1:1. Gong, et al., *supra*. NK-92 cells are deposited with the American Type Culture Collection (ATCC), designation CRL-2407.

Heretofore, studies on endogenous NK cells have indicated that IL-2 (1000 IU/mL) is critical for NK cell activation during shipment, but that the cells need not be maintained at 37° C. and 5% carbon dioxide. Koepsell, et al., *Transfusion* 53:398-403 (2013).

Modified NK-92 cells are known and include, but are not limited to, those described in, e.g., U.S. Pat. Nos. 7,618,817, 8,034,332, and 8,313,943, US Patent Application Publication No. 2013/0040386, all of which are incorporated herein by reference in their entireties, such as wild type NK-92, NK-92-CD16, NK-92-CD16-γ, NK-92-CD16-ζ, NK-92-CD16(F157V), NK-92mi and NK-92ci.

Although NK-92 cells retain almost all of the activating receptors and cytolytic pathways associated with NK cells, they do not express CD16 on their cell surfaces. CD16 is an Fc receptor which recognizes and binds to the Fc portion of an antibody to activate NK cells for antibody-dependent cellular cytotoxicity (ADCC). Due to the absence of CD16 receptors, NK-92 cells are unable to lyse target cells via the ADCC mechanism and, as such, cannot potentiate the anti-tumor effects of endogenous or exogenous antibodies (i.e., Rituximab and Herceptin).

Studies on endogenous NK cells have indicated that IL-2 (1000 IU/mL) is critical for NK cell activation during shipment, but that the cells need not be maintained at 37° C. and 5% carbon dioxide. Koepsell, et al., Transfusion 53:398-403 (2013). However, endogenous NK cells are significantly different from NK-92 cells, in large part because of their distinct origins: NK-92 is a cancer-derived cell line, whereas endogenous NK cells are harvested from a donor (or the patient) and processed for infusion into a patient. Endogenous NK cell preparations are heterogeneous cell populations, whereas NK-92 cells are a homogeneous, clonal cell line. NK-92 cells readily proliferate in culture while maintaining cytotoxicity, whereas endogenous NK cells do not. In addition, an endogenous heterogeneous population of NK cells does not aggregate at high density. Furthermore, endogenous NK cells express Fc receptors, including CD-16 receptors that are not expressed by NK-92 cells.

Fc Receptors

Fc receptors bind to the Fc portion of antibodies. Several Fc receptors are known, and differ according to their preferred ligand, affinity, expression, and effect following binding to the antibody.

TABLE 1

Illustrative Fc receptors

| Receptor name | Principal antibody ligand | Affinity for ligand | Cell distribution | Effect following binding to antibody |
|---|---|---|---|---|
| FcγRI (CD64) | IgG1 and IgG3 | High (Kd ~10$^{-9}$M) | Macrophages Neutrophils Eosinophils Dendritic cells | Phagocytosis Cell activation Activation of respiratory burst Induction of microbe killing |
| FcγRIIA (CD32) | IgG | Low (Kd >10$^{-7}$M) | Macrophages Neutrophils Eosinophils Platelets Langerhans cells | Phagocytosis Degranulation (eosinophils) |
| FcγRIIB1 (CD32) | IgG | Low (Kd >10$^{-7}$M) | B Cells Mast cells | No phagocytosis Inhibition of cell activity |
| FcγRIIB2 (CD32) | IgG | Low (Kd >10$^{-7}$M) | Macrophages Neutrophils Eosinophils | Phagocytosis Inhibition of cell activity |
| FcγRIIIA (CD16a) | IgG | Low (Kd >10$^{-6}$M) | NK cells Macrophages (certain tissues) | Induction of antibody-dependent cell-mediated cytotoxicity (ADCC) Induction of cytokine release by macrophages |
| FcγRIIIB (CD16b) | IgG | Low (Kd >10$^{-6}$M) | Eosinophils Macrophages Neutrophils Mast cells Follicular dendritic cells | Induction of microbe killing |
| FcεRI | IgE | High (Kd ~10$^{-10}$M) | Mast cells Eosinophils Basophils Langerhans cells Monocytes | Degranulation Phagocytosis |

TABLE 1-continued

Illustrative Fc receptors

| Receptor name | Principal antibody ligand | Affinity for ligand | Cell distribution | Effect following binding to antibody |
|---|---|---|---|---|
| FcεRII (CD23) | IgE | Low (Kd >$10^{-7}$M) | B cells Eosinophils Langerhans cells | Possible adhesion molecule IgE transport across human intestinal epithelium Positive-feedback mechanism to enhance allergic sensitization (B cells) |
| FcαRI (CD89) | IgA | Low (Kd >$10^{-6}$M) | Monocytes Macrophages Neutrophils Eosinophils | Phagocytosis Induction of microbe killing |
| Fcα/μR | IgA and IgM | High for IgM Mid for IgA | B cells Mesangial cells Macrophages | Endocytosis Induction of microbe killing |
| FcRn | IgG | | Monocytes Macrophages Dendritic cells Epithelial cells Endothelial cells Hepatocytes | Transfers IgG from a mother to fetus through the placenta Transfers IgG from a mother to infant in milk Protects IgG from degradation |

In some embodiments NK-92 cells are modified to express an Fc receptor protein on the cell surface.

In some embodiments, the Fc receptor is CD16. For purposes of this disclosure, specific amino acid residues of CD16 are designated with reference to SEQ ID NO: 2, or to SEQ ID NO: 1, which differs at one position relative to SEQ ID NO: 2. Thus, an amino acid residue "at position 158" of a CD16 polypeptide is the amino acid residue that corresponds to position 158 of SEQ ID NO: 2 (or SEQ ID NO: 1), when the CD16 polypeptide and SEQ ID NO: 2 are maximally aligned. In some embodiments, NK-92 cells are modified to express a human CD16 that has a phenylalanine at position 158 of the mature form of the protein, e.g., SEQ ID NO: 1. In typical embodiments, NK-92 cells are modified to express a high affinity form of human CD16 having a valine at position 158 of the mature form of the protein, e.g., SEQ ID NO: 2. Position 158 of the mature protein corresponds to position 176 of the CD16 sequence that includes the native signal peptide. In some embodiments, a CD16 polypeptide is encoded by a polynucleotide that encodes the precursor (i.e., has a native signal peptide) polypeptide sequence of SEQ ID NO: 3 or of SEQ ID NO: 4.

In some embodiments, a polynucleotide encoding a CD16 polypeptide has at least about 70% polynucleotide sequence identity with a polynucleotide sequence encoding a full-length, including signal peptide, naturally occurring CD16 that has a phenylalanine at position 176 of the full-length CD16 (which corresponds to position 158 of the mature CD16 protein). In some embodiments, a polynucleotide encoding a CD16 polypeptide has at least about 70% polynucleotide sequence identity with a polynucleotide sequence encoding a full-length, including the signal peptide, naturally occurring CD16 that has a valine at position 176 (which corresponds to position 158 of the mature protein). In some embodiments, a polynucleotide encoding CD16 has at least 70% identity to SEQ ID NO: 5 and comprises a codon encoding valine at the position of the polynucleotide that encodes position 176 of the full-length, including the signal peptide, CD16 polypeptide. In some embodiments, a polynucleotide encoding CD16 has at least 90% identity to SEQ ID NO: 5 and comprises a codon encoding valine at position 176 of the full-length CD16. In some embodiments, a polynucleotide encoding CD16 comprises SEQ ID NO: 5, but with a codon encoding valine at position 176 of the full-length CD16.

In some embodiments, the CD16 polynucleotide encodes a polypeptide having at least 70%, 80%, 90%, or 95% identity to SEQ ID NO: 1 or SEQ ID NO: 2. In some embodiments, the polynucleotide encodes a polypeptide having at least 70% identity, or at least 80% identity, to SEQ ID NO: 2 and comprises a valine at position 158 as determined with reference to SEQ ID NO: 2. In some embodiments, the polynucleotide encodes a polypeptide having at least 90% identity to SEQ ID NO: 2 and comprises a valine at position 158 as determined with reference to SEQ ID NO: 2. In some embodiments, the polynucleotide encodes a polypeptide having at least 95% identity to SEQ ID NO: 2 and comprises a valine at position 2 as determined with reference to SEQ ID NO: 2. In some embodiments the polynucleotide encodes SEQ ID NO: 2. In some embodiments, a CD16 polynucleotide encodes an extracellular domain of CD16 with or without the signal sequence, or any other fragment of a full length CD16, or a chimeric receptor encompassing at least partial sequence of CD16 fused to an amino acid sequence of another protein. In other embodiments, an epitope tag peptide, such as FLAG, myc, poly-histidine, or V5 can be added to the amino terminal domain of the mature polypeptide to assist in cell surface detection by using anti-epitope tag peptide monoclonal or polyclonal antibodies.

In some embodiments, homologous CD16 polynucleotides may be about 150 to about 700, about 750, or about 800 polynucleotides in length, although CD16 variants having more than 700 to 800 polynucleotides are within the scope of the disclosure.

Homologous polynucleotide sequences include those that encode polypeptide sequences coding for variants of CD16. Homologous polynucleotide sequences also include naturally occurring allelic variations related to SEQ ID NO: 5. Transfection of an NK-92 cell with any polynucleotide encoding a polypeptide having the amino acid sequence shown in either SEQ ID. NO: 1 or SEQ ID NO: 2, a naturally occurring variant thereof, or a sequence that is at least 70% identical, or at least 80%, 90%, or 95% identical to SEQ ID. NO: 1 or SEQ ID NO: 2 is within the scope of the disclosure. In some embodiments, homologous polynucleotide sequences encode conservative amino acid substitutions in SEQ ID. NO: 1 or SEQ ID NO: 2. In some embodiments, NK-92 cells are transfected using a degenerate homologous CD16 polynucleotide sequence that differs from a native polynucleotide sequence, but encodes the same polypeptide.

In other examples, cDNA sequences having polymorphisms that change the CD16 amino acid sequences are used to modify the NK-92 cells, such as, for example, the allelic variations among individuals that exhibit genetic polymorphisms in CD16 genes. In other examples, CD16 genes from other species that have a polynucleotide sequence that differs from the sequence of SEQ ID NO: 5 are used to modify NK-92 cells.

In examples, variant polypeptides are made using methods known in the art such as oligonucleotide-mediated (site-directed) mutagenesis, alanine scanning, and PCR mutagenesis. Site direct mutagenesis (Carter, 1986; Zoller and Smith, 1987), cassette mutagenesis, restriction selection mutagenesis (Wells et al., 1985) or other known techniques can be performed on the cloned DNA to produce CD16 variants (Ausubel, 2002; Sambrook and Russell, 2001).

In some embodiments, a polynucleotide encoding a CD16 is mutated to alter the amino acid sequence encoding for CD16 without altering the function of CD16. For example, polynucleotide substitutions leading to amino acid substitutions at "non-essential" amino acid residues can be made in SEQ ID NO: 1 or SEQ ID NO: 2.

Conservative substitutions in SEQ ID. NO: 1 or SEQ ID NO: 2, whereby an amino acid of one class is replaced with another amino acid of the same class, fall within the scope of the disclosed CD16 variants as long as the substitution does not materially alter the activity of the polypeptide. Conservative substitutions are well known to one of skill in the art. Non-conservative substitutions that affect (1) the structure of the polypeptide backbone, such as a β-sheet or α-helical conformation, (2) the charge, (3) the hydrophobicity, or (4) the bulk of the side chain of the target site can modify CD16 polypeptide function or immunological identity. Non-conservative substitutions entail exchanging a member of one of these classes for another class. Substitutions may be introduced into conservative substitution sites or more preferably into non-conserved sites.

In some embodiments, CD16 polypeptide variants are at least 200 amino acids in length and have at least 70% amino acid sequence identity, or at least 80%, or at least 90% identity to SEQ ID NO: 1 or SEQ ID NO: 2. In some embodiments, CD16 polypeptide variants are at least 225 amino acid in length and have at least 70% amino acid sequence identity, or at least 80%, or at least 90% identity to SEQ ID NO: 1 or SEQ ID NO: 2. In some embodiments, CD16 polypeptide variants have a valine at position 158 as determined with reference to SEQ ID NO: 2.

In some embodiments a nucleic acid encoding a CD16 polypeptide may encode a CD16 fusion protein. A CD16 fusion polypeptide includes any portion of CD16 or an entire CD16 fused with a non-CD16 polypeptide. Fusion polypeptides are conveniently created using recombinant methods. For example, a polynucleotide encoding a CD16 polypeptide such as SEQ ID NO: 1 or SEQ ID NO: 2 is fused in-frame with a non-CD16 encoding polynucleotide (such as a polynucleotide sequence encoding a signal peptide of a heterologous protein). In some embodiment, a fusion polypeptide may be created in which a heterologous polypeptide sequence is fused to the C-terminus of CD16 or is positioned internally in the CD16. Typically, up to about 30% of the CD16 cytoplasmic domain may be replaced. Such modification can enhance expression or enhance cytotoxicity (e.g., ADCC responsiveness). In other examples, chimeric proteins, such as domains from other lymphocyte activating receptors, including but not limited to Ig-a, Ig-B, CD3-e, CD3-d, DAP-12 and DAP-10, replace a portion of the CD16 cytoplasmic domain.

Fusion genes can be synthesized by conventional techniques, including automated DNA synthesizers and PCR amplification using anchor primers that give rise to complementary overhangs between two consecutive gene fragments that can subsequently be annealed and reamplified to generate a chimeric gene sequence (Ausubel, 2002). Many vectors are commercially available that facilitate sub-cloning CD16 in-frame to a fusion moiety.

Chimeric Antigen Receptor

As described herein, NK-92 cells are further engineered to express a chimeric antigen receptor (CAR) on the cell surface. Optionally, the CAR is specific for a tumor-specific antigen. Tumor-specific antigens are described, by way of non-limiting example, in US 2013/0189268; WO 1999024566 A1; U.S. Pat. No. 7,098,008; and WO 2000020460 A1, each of which is incorporated herein by reference in its entirety. Tumor-specific antigens include, without limitation, NKG2D, CS1, GD2, CD138, EpCAM, EBNA3C, GPA7, CD244, CA-125, ETA, MAGE, CAGE, BAGE, HAGE, LAGE, PAGE, NY-SEO-1, GAGE, CEA, CD52, CD30, MUC5AC, c-Met, EGFR, FAB, WT-1, PSMA, NY-ESO1, AFP, CEA, CTAG1B, CD19 and CD33. Additional non-limiting tumor-associated antigens, and the malignancies associated therewith, can be found in Table 1.

TABLE 1

Tumor-Specific Antigens and Associated Malignancies

| Target Antigen | Associated Malignancy |
|---|---|
| α-Folate Receptor | Ovarian Cancer |
| CAIX | Renal Cell Carcinoma |
| CD19 | B-cell Malignancies |
| | Chronic lymphocytic leukemia (CLL) |
| | B-cell CLL (B-CLL) |
| | Acute lymphoblastic leukemia (ALL); ALL post Hematopoietic stem cell transplantation (HSCT) |
| | Lymphoma; Refractory Follicular Lymphoma; B-cell non-Hodgkin lymphoma (B-NHL) |
| | Leukemia |
| | B-cell Malignancies post-HSCT |
| | B-lineage Lymphoid Malignancies post umbilical cord blood transplantation (UCBT) |
| CD19/CD20 | Lymphoblastic Leukemia |
| CD20 | Lymphomas |
| | B-Cell Malignancies |
| | B-cell Lymphomas |
| | Mantle Cell Lymphoma |
| | Indolent B-NHL |
| | Leukemia |
| CD22 | B-cell Malignancies |
| CD30 | Lymphomas; Hodgkin Lymphoma |
| CD33 | AML |
| CD44v7/8 | Cervical Carcinoma |
| CD138 | Multiple Myeloma |
| CD244 | Neuroblastoma |
| CEA | Breast Cancer |
| | Colorectal Cancer |
| CS1 | Multiple Myeloma |

TABLE 1-continued

Tumor-Specific Antigens and Associated Malignancies

| Target Antigen | Associated Malignancy |
| --- | --- |
| EBNA3C | EBV Positive T-cells |
| EGP-2 | Multiple Malignancies |
| EGP-40 | Colorectal Cancer |
| EpCAM | Breast Carcinoma |
| Erb-B2 | Colorectal Cancer |
|  | Breast Cancer and Others |
|  | Prostate Cancer |
| Erb-B 2, 3, 4 | Breast Cancer and Others |
| FBP | Ovarian Cancer |
| Fetal Acetylcholine Receptor | Rhabdomyosarcoma |
| GD2 | Neuroblastoma |
| GD3 | Melanoma |
| GPA7 | Melanoma |
| Her2 | Breast Carcinoma |
|  | Ovarian Cancer |
|  | Tumors of Epithelial Origin |
| Her2/new | Medulloblastoma |
|  | Lung Malignancy |
|  | Advanced Osteosarcoma |
|  | Glioblastoma |
| IL-13R-a2 | Glioma |
|  | Glioblastoma |
|  | Medulloblastoma |
| KDR | Tumor Neovasculature |
| k-light chain | B-cell Malignancies |
|  | B-NHL, CLL |
| LeY | Carcinomas |
|  | Epithelial Derived Tumors |
| L1 Cell Adhesion Molecule | Neuroblastoma |
| MAGE-A1 | Melanoma |
| Mesothelin | Various Tumors |
| MUC1 | Breast Cancer; Ovarian Cancer |
| NKG2D Ligands | Various Tumors |
| Oncofetal Antigen (h5T4) | Various Tumors |
| PSCA | Prostate Carcinoma |
| PSMA | Prostate/Tumor Vasculature |
| TAA Targeted by mAb IgE | Various Tumors |
| TAG-72 | Adenocarcinomas |
| VEGF-R2 | Tumor Neovasculature |

In some embodiments, the CAR targets CD19, CD33 or CSPG-4. Representative polynucleotide and polypeptide sequences for the CD19, CD33 and CSPG-4 CARs are provided in SEQ ID NO: 8 (CD19 CAR polynucleotide), SEQ ID NO: 9 (CD19 CAR polypeptide), SEQ ID NO: 10 (CD33 CAR polynucleotide), SEQ ID NO: 11 (CD33 CAR polypeptide), SEQ ID NO: 12 (CSPG-4 CAR polynucleotide), and SEQ ID NO: 13 (CSPG-4 CAR polypeptide). In some embodiments, the CD19 CAR polynucleotide encodes a polypeptide having at least 70%, 80%, 90%, or 95% identity to SEQ ID NO: 9. Optionally, the CD19 CAR polypeptide has at least 90, 91, 92, 93, 94, 95, 96, 97, 98, or 99% identity to SEQ ID NO: 9. In some embodiments, the CD33 CAR polynucleotide encodes a polypeptide having at least 70%, 80%, 90%, or 95% identity to SEQ ID NO: 11. Optionally, the CD33 CAR polypeptide has at least 90, 91, 92, 93, 94, 95, 96, 97, 98, or 99% identity to SEQ ID NO: 11. In some embodiments, the CSPG-4 CAR polynucleotide encodes a polypeptide having at least 70%, 80%, 90%, or 95% identity to SEQ ID NO: 13. Optionally, the CSPG-4 CAR polypeptide has at least 90, 91, 92, 93, 94, 95, 96, 97, 98, or 99% identity to SEQ ID NO: 13. In some embodiments, an epitope tag peptide, such as FLAG, myc, polyhistidine, or V5 can be added to the amino terminal domain of the polypeptide to assist in cell surface detection by using anti-epitope tag peptide monoclonal or polyclonal antibodies.

In examples, variant polypeptides are made using methods known in the art such as oligonucleotide-mediated (site-directed) mutagenesis, alanine scanning, and PCR mutagenesis. Site direct mutagenesis (Carter, 1986; Zoller and Smith, 1987), cassette mutagenesis, restriction selection mutagenesis (Wells et al., 1985) or other known techniques can be performed on the cloned DNA to produce CD16 variants (Ausubel, 2002; Sambrook and Russell, 2001).

In some embodiments, a polynucleotide encoding a CAR is mutated to alter the amino acid sequence encoding for CAR without altering the function of the CAR. For example, polynucleotide substitutions leading to amino acid substitutions at "non-essential" amino acid residues can be made in SEQ ID NO: 9, SEQ ID NO: 11 or SEQ ID NO: 13.

Conservative substitutions in SEQ ID NO: 9, SEQ ID NO: 11 or SEQ ID NO: 13, whereby an amino acid of one class is replaced with another amino acid of the same class, fall within the scope of the disclosed variants as long as the substitution does not materially alter the activity of the polypeptide. Conservative substitutions are well known to one of skill in the art. Non-conservative substitutions that affect (1) the structure of the polypeptide backbone, such as a β-sheet or α-helical conformation, (2) the charge, (3) the hydrophobicity, or (4) the bulk of the side chain of the target site can modify polypeptide function or immunological identity. Non-conservative substitutions entail exchanging a member of one of these classes for another class. Substitutions may be introduced into conservative substitution sites or more preferably into non-conserved sites.

Optionally, the CAR targets an antigen associated with a specific cancer type. Optionally, the cancer is selected from the group consisting of leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia), polycythemia vera, lymphomas (e.g., Hodgkin's disease and non-Hodgkin's disease), multiple myeloma, Waldenstrom's macroglobulinemia, heavy chain disease, solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

CARs can be engineered as described, for example, in Patent Publication Nos. WO 2014039523; US 20140242701; US 20140274909; US 20130280285; and WO 2014099671, each of which is incorporated herein by reference in its entirety. Optionally, the CAR is a CD19 CAR, a CD33 CAR or CSPG-4 CAR.

Additional Modifications—Cytokines

The cytotoxicity of NK-92 cells is dependent on the presence of cytokines (e.g., interleukin-2 (IL-2)). The cost of using exogenously added IL-2 needed to maintain and expand NK-92 cells in commercial scale culture is significant. The administration of IL-2 to human subjects in sufficient quantity to continue activation of NK92 cells would cause adverse side effects.

In some embodiments, FcR-expressing NK-92 cells are further modified to express at least one cytokine and a suicide gene. In specific embodiments, the at least one cytokine is IL-2, IL-12, IL-15, IL-18, IL-21 or a variant thereof. In preferred embodiments, the cytokine is IL-2 (SEQ ID NO: 6). In certain embodiments the IL-2 is a variant that is targeted to the endoplasmic reticulum, and the suicide gene is iCas9.

In one embodiment, the IL-2 is expressed with a signal sequence that directs the IL-2 to the endoplasmic reticulum. In some embodiments, a polynucleotide that encodes IL-2 encodes a polypeptide having a sequence of SEQ ID NO: 7. Not to be bound by theory, but directing the IL-2 to the endoplasmic reticulum permits expression of IL-2 at levels sufficient for autocrine activation, but without releasing IL-2 extracellularly. See Konstantinidis et al "Targeting IL-2 to the endoplasmic reticulum confines autocrine growth stimulation to NK-92 cells" *Exp Hematol.* 2005 February; 33(2): 159-64. Continuous activation of the FcR-expressing NK-92 cells can be prevented, e.g., by the presence of the suicide gene.

Additional Modifications—Suicide Gene

The term "suicide gene" is one that allows for the negative selection of the cells. A suicide gene is used as a safety system, allowing the cells expressing the gene to be killed by introduction of a selective agent. This is desirable in case the recombinant gene causes a mutation leading to uncontrolled cell growth. A number of suicide gene systems have been identified, including the herpes simplex virus thymidine kinase (TK) gene, the cytosine deaminase gene, the varicella-zoster virus thymidine kinase gene, the nitroreductase gene, the *Escherichia coli* gpt gene, and the *E. coli* Deo gene (also see, for example, Yazawa K, Fisher W E, Brunicardi F C: Current progress in suicide gene therapy for cancer. World J. Surg. 2002 July; 26(7):783-9). As used herein, the suicide gene is active in NK-92 cells. Typically, the suicide gene encodes for a protein that has no ill-effect on the cell but, in the presence of a specific compound, will kill the cell. Thus, the suicide gene is typically part of a system.

In one embodiment, the suicide gene is the thymidine kinase (TK) gene. The TK gene may be a wild-type or mutant TK gene (e.g., tk30, tk75, sr39tk). Cells expressing the TK protein can be killed using ganciclovir.

In another embodiment, the suicide gene is Cytosine deaminase which is toxic to cells in the presence of 5-fluorocytosine. Garcia-Sanchez et al. "Cytosine deaminase adenoviral vector and 5-fluorocytosine selectively reduce breast cancer cells 1 million-fold when they contaminate hematopoietic cells: a potential purging method for autologous transplantation." *Blood* 1998 Jul. 15; 92(2):672-82.

In another embodiment, the suicide gene is cytochrome P450 which is toxic in the presence of ifosfamide, or cyclophosphamide. See e.g. Touati et al. "A suicide gene therapy combining the improvement of cyclophosphamide tumor cytotoxicity and the development of an anti-tumor immune response." *Curr Gene Ther.* 2014; 14(3):236-46.

In another embodiment, the suicide gene is iCas9. Di Stasi, (2011) "Inducible apoptosis as a safety switch for adoptive cell therapy." N Engl J Med 365: 1673-1683. See also Morgan, "Live and Let Die: A New Suicide Gene Therapy Moves to the Clinic" *Molecular Therapy* (2012); 20: 11-13. The iCas9 protein induces apoptosis in the presence of a small molecule AP1903. AP1903 is biologically inert small molecule, that has been shown in clinical studies to be well tolerated, and has been used in the context of adoptive cell therapy.

In one embodiment, the modified NK-92 cells are irradiated prior to administration to the patient. Irradiation of NK-92 cells is described, for example, in U.S. Pat. No. 8,034,332, which is incorporated herein by reference in its entirety. In one embodiment, modified NK-92 cells that have not been engineered to express a suicide gene are irradiated.

Transgene Expression

Transgenes (e.g., CD19 CAR and CD16) can be engineered into an expression vector by any mechanism known to those of skill in the art. Transgenes may be engineered into the same expression vector or a different expression vector. In preferred embodiments, the transgenes are engineered into the same vector.

In some embodiments, the vector allows incorporation of the transgene(s) into the genome of the cell. In some embodiments, the vectors have a positive selection marker. Positive selection markers include any genes that allow the cell to grow under conditions that would kill a cell not expressing the gene. Non-limiting examples include antibiotic resistance, e.g., geneticin (Neo gene from Tn5).

Any number of vectors can be used to express the Fc receptor and/or the CAR. In some embodiments, the vector is a plasmid. In one embodiment, the vector is a viral vector. Viral vectors include, but are not limited to, retroviral vectors, adenoviral vectors, adeno-associated viral vectors, herpes simplex viral vectors, pox viral vectors, and others.

Transgenes can be introduced into the NK-92 cells using any transfection method known in the art, including, by way of non-limiting example, infection, electroporation, lipofection, nucleofection, or "gene-gun."

Antibodies

Optionally, antibodies may be used to target cancerous cells or cells that express cancer-associated markers. A number of antibodies have been approved for the treatment of cancer, alone.

TABLE 2

Example FDA approved therapeutic monoclonal antibodies

| Antibody | Brand name | Company | Target | Indication (Targeted disease) |
|---|---|---|---|---|
| Alemtuzumab | Campath ® | Genzyme | CD52 | Chronic lymphocytic leukemia |
| Brentuximab vedotin | Adcetris ® | | CD30 | Anaplastic large cell lymphoma (ALCL) and Hodgkin lymphoma |
| Cetuximab | Erbitux ® | Bristol-Myers Squibb/Eli | epidermal growth factor receptor | Colorectal cancer, Head and neck cancer |

TABLE 2-continued

Example FDA approved therapeutic monoclonal antibodies

| Antibody | Brand name | Company | Target | Indication (Targeted disease) |
|---|---|---|---|---|
| Gemtuzumab | Mylotarg ® | Lilly/Merck KGaA Wyeth | CD33 | Acute myelogenous leukemia (with calicheamicin) |
| Ibritumomab tiuxetan | Zevalin ® | Spectrum Pharmaceuticals, Inc. | CD20 | Non-Hodgkin lymphoma (with yttrium-90 or indium-111) |
| Ipilimumab (MD X-101) | Yervoy ® | | blocks CTLA-4 | Melanoma |
| Ofatumumab | Arzerra ® | | CD20 | Chronic lymphocytic leukemia |
| Palivizumab | Synagis ® | MedImmune | an epitope of the RSV F protein | Respiratory Syncytial Virus |
| Panitumumab | Vectibix ® | Amgen | epidermal growth factor receptor | Colorectal cancer |
| Rituximab | Rituxan ®, Mabthera ® | Biogen Idec/Genentech | CD20 | Non-Hodgkin lymphoma |
| Tositumomab | Bexxar ® | GlaxoSmithKline | CD20 | Non-Hodgkin lymphoma |
| Trastuzumab | Herceptin ® | Genentech | ErbB2 | Breast cancer |
| Blinatunomab | | | bispecific CD19-directed CD3 T-cell engager | Philadelphia chromosome-negative relapsed or refractory B cell precursor acute lymphoblastic leukemia (ALL) |
| Avelumamab | | | anti-PD-L1 | Non-small cell lung cancer, metastatic Merkel cell carcinoma; gastic cancer, breast cancer, ovarian cancer, bladder cancer, melanoma, meothelioma, including metastatic or locally advanced solid tumors |
| Daratumumab | | | CD38 | Multiple myeloma |
| Elotuzumab | | | a SLAMF7-directed (also known as CD 319) immunostimulatory antibody | Multiple myeloma |

Antibodies may treat cancer through a number of mechanisms. Antibody-dependent cellular cytotoxicity (ADCC) occurs when immune cells, such as NK cells, bind to antibodies that are bound to target cells through Fc receptors, such as CD16.

Accordingly, in some embodiments, NK-92 cells that express CD16 and/or a CAR are administered to a patient along with an effective amount of at least one monoclonal antibody directed against a specific cancer-associated protein, for example, alemtuzumab, bevacizumab, ibritumomab tiuxetan, ofatumumab, rituximab, and trastuzumab. In some embodiments, the monoclonal antibody is a naked monoclonal antibody, a conjugated monoclonal antibody or a bispecific monoclonal antibody. In one embodiment, a bispecific antibody can be used that binds the cancer cell and also binds a cell-surface protein present on the surface of NK-92 cells.

Cancer-specific antibodies bind to particular protein antigens that are expressed on the surfaces of cancer cells. NK-92 cells can be modified such that an antibody is associated with the NK-92 cell surface. In a preferred embodiment, the antibody is specific for the cancer. In this way, the NK-92 cell can be specifically targeted to the cancer. Neutralizing antibodies may also be isolated. For example, a secreted glycoprotein, YKL-40, is elevated in multiple types of advanced human cancers. It is contemplated that an antibody to YKL-40 could be used to restrain tumor growth, angiogenesis and/or metastasis. Faibish et al., (2011) Mol. Cancer Ther. 10(5):742-751.

The antibody can be administered in conjunction with administration of NK-92 cells. An antibody specific for the cancer to be treated can be administered prior to, concurrently with, and/or after administration of the NK-92 cells.

Antibodies to cancer can be purchased from commercially available sources or can be produced by any method known in the art. For example, antibodies can be produced by obtaining B cells, bone marrow, or other samples from previously one or more patients who were infected by the cancer and recovered or were recovering when the sample was taken. Methods of identifying, screening, and growing antibodies (e.g., monoclonal antibodies) from these samples are known. For example, a phage display library can be made by isolating RNA from the sample or cells of interest, preparing cDNA from the isolated RNA, enriching the cDNA for heavy-chain and/or light-chain cDNA, and creating libraries using a phage display vector. Libraries can be prepared and screened as described, for example, in Maruyama, et al., which is incorporated herein by reference in its entirety. Antibodies can be made by recombinant methods or any other method. Isolation, screening, characterization, and production of human monoclonal antibodies are also described in Beerli, et al., PNAS (2008) 105(38): 14336-14341, which is incorporated herein by reference in its entirety.

Treatment

Also provided are methods of treating patients with modified NK-92 cells as described herein. In one embodiment, the patient is suffering from cancer and the CAR expressed by the NK-92 cell is specific for an antigen expressed on the surface of that cancer. The NK-92 expresses an Fc receptor in addition to a CAR specific for an antigen expressed on the surface of that cancer (i.e., NK-92-Fc-CAR). For example, the NK-92 cell could express CD16 and MAGE on its cell surface (i.e., NK-92-CD16-MAGE). Optionally, the patient is treated with the modified NK92 cell and also an antibody.

NK-92 cells can be administered to an individual by absolute numbers of cells, e.g., said individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) NK-92 cells per injection, or any ranges between any two of the numbers, end points inclusive.

In other embodiments, said individual can be administered from about 1000 cells/injection/$m^2$ to up to about 10 billion cells/injection/$m^2$, such as at about, at least about, or at most about, $1\times10^8/m^2$, $1\times10^7/m^2$, $5\times10^7/m^2$, $1\times10^6/m^2$, $5\times10^6/m^2$, $1\times10^5/m^2$, $5\times10^5/m^2$, $1\times10^4/m^2$, $5\times10^4/m^2$, $1\times10^3/m^2$, $5\times10^3/m^2$ (and so forth) NK-92 cells per injection, or any ranges between any two of the numbers, end points inclusive.

In other embodiments, NK-92 cells can be administered to such individual by relative numbers of cells, e.g., said individual can be administered about 1000 cells to up to about 10 billion cells per kilogram of the individual, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) NK-92 cells per kilogram of the individual, or any ranges between any two of the numbers, end points inclusive.

In other embodiments, the total dose may calculated by $m^2$ of body surface area, including about $1\times10^{11}$, $1\times10^{10}$, $1\times10^9$, $1\times10^8$, $1\times10^7$, per $m^2$, or any ranges between any two of the numbers, end points inclusive. The average person is about 1.6 to about 1.8 $m^2$. In a preferred embodiment, between about 1 billion and about 3 billion NK-92 cells are administered to a patient. In other embodiments, the amount of NK-92 cells injected per dose may calculated by $m^2$ of body surface area, including $1\times10^{11}$, $1\times10^1$, $1\times10^9$, $1\times10^8$, $1\times10^7$, per $m^2$. The average person is 1.6-1.8 $m^2$.

The NK-92 cells, and optionally other anti-cancer agents can be administered once to a patient with cancer can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In some embodiments, NK-92 cells are administered in a composition comprising NK-92 cells and a medium, such as human serum or an equivalent thereof. In some embodiments, the medium comprises human serum albumin. In some embodiments, the medium comprises human plasma. In some embodiments, the medium comprises about 1% to about 15% human serum or human serum equivalent. In some embodiments, the medium comprises about 1% to about 10% human serum or human serum equivalent. In some embodiments, the medium comprises about 1% to about 5% human serum or human serum equivalent. In a preferred embodiment, the medium comprises about 2.5% human serum or human serum equivalent. In some embodiments, the serum is human AB serum. In some embodiments, a serum substitute that is acceptable for use in human therapeutics is used instead of human serum. Such serum substitutes may be known in the art, or developed in the future. Although concentrations of human serum over 15% can be used, it is contemplated that concentrations greater than about 5% will be cost-prohibitive. In some embodiments, NK-92 cells are administered in a composition comprising NK-92 cells and an isotonic liquid solution that supports cell viability. In some embodiments, NK-92 cells are administered in a composition that has been reconstituted from a cryopreserved sample.

Pharmaceutically acceptable compositions can include a variety of carriers and excipients. A variety of aqueous carriers can be used, e.g., buffered saline and the like. These solutions are sterile and generally free of undesirable matter. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. As used herein, the term pharmaceutically acceptable is used synonymously with physiologically acceptable and pharmacologically acceptable. A pharmaceutical composition will generally comprise agents for buffering and preservation in storage and can include buffers and carriers for appropriate delivery, depending on the route of administration.

These compositions for use in in vivo or in vitro may be sterilized by conventional, well-known sterilization techniques. The compositions may contain acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of cells in these formulations and/or other agents can vary and will be selected primarily based on fluid volumes, viscosities, body weight and the like in accordance with the particular mode of administration selected and the subject's needs.

In one embodiment, the NK-92 cells are administered to the patient in conjunction with one or more other treatments for the cancer being treated. Without being bound by theory, it is believed that co-treatment of a patient with NK-92 cells and another therapy for the cancer will allow the NK-92 cells and the alternative therapy to give the endogenous immune system a chance to clear the cancer that heretofore had overwhelmed such endogenous action. In some embodiments, two or more other treatments for the cancer being treated includes, for example, an antibody, radiation, chemotherapeutic, stem cell transplantation, or hormone therapy.

In one embodiment, an antibody is administered to the patient in conjunction with the NK-92 cells. In one embodiment, the NK-92 cells and an antibody are administered to the patient together, e.g., in the same formulation; separately, e.g., in separate formulations, concurrently; or can be administered separately, e.g., on different dosing schedules or at different times of the day. When administered separately, the antibody can be administered in any suitable route, such as intravenous or oral administration.

Without being bound by theory, it is contemplated that the NK-92 cells expressing a combination of an Fc receptor and a CAR and when administered with a monoclonal antibody will more readily anticipate escape mutants, and also, avoid selecting for escape mutants. In addition, a patient's own effector cells may participate in ADCC with the monoclonal antibody to target cancer cells. This dual system (both an Fc receptor and a CAR) may also be more selective for cancer cells than non-cancerous cells (off-tumor on-target). Few tumor associated antigens are exclusively expressed on cancer cells, but it is rare that a non-cancerous cell would overexpress two tumor associated/specific antigens. For example, lymphocytes usually express both CD19 and CD20, often one being upregulated while the other is down regulated and vice versa. A NK-92-CD16-CD19 in combination with ibritumomab tiuxetan or rituximab could be effective in treating certain lymphomas.

Kits

Also disclosed are kits for the treatment of cancer using compositions comprising an amount of NK-92 cells that are modified to express at least one Fc receptor on a cell surface and at least one a chimeric antigen receptor (CAR) on the cell surface and instructions for use in the treatment of cancer. In some embodiments, the kits of the present disclosure may also include at least one monoclonal antibody.

The components of the kit may be contained in one or different containers such as one or more vials. The antibody may be in liquid or solid form (e.g., after lyophilization) to enhance shelf-life. If in liquid form, the components may comprise additives such as stabilizers and/or preservatives such as proline, glycine, or sucrose or other additives that enhance shelf-life.

In certain embodiments, the kit may contain additional compounds such as therapeutically active compounds or drugs that are to be administered before, at the same time or after administration of the modified NK-92 cells or NK-92 cells and antibody. Examples of such compounds include vitamins, minerals, fludrocortisone, ibuprofen, lidocaine, quinidine, chemotherapeutic, etc.

In various embodiments, instructions for use of the kits will include directions to use the kit components in the treatment of a cancer. The instructions may further contain information regarding how to prepare (e.g., dilute or reconstitute, in the case of freeze-dried protein) the antibody and the NK-92 cells (e.g., thawing and/or culturing). The instructions may further include guidance regarding the dosage and frequency of administration.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

EXAMPLES

The following examples are for illustrative purposes only and should not be interpreted as limitations. There are a variety of alternative techniques and procedures available to those of skill in the art which would similarly permit one to successfully perform the examples below.

Example 1: Prolonged Survival Following Treatment with an NK-92-Fc-CAR

CD19-positive leukemic cells derived from a T-lineage-acute lymphoblastic leukemia (ALL) patient, an acute myeloid leukemia (AML) patient, and a pre-B-ALL patient are adoptively grown and expanded in NSG mice by S.C. inoculation. Leukemic cells recovered from the leukemic nodules in the mice (first passage) are used. The NSG mice in each group are inoculated I.P. with $5 \times 10^6$ leukemic cells from the first passage in 0.2 mL PBS. All the human leukemias grow aggressively in NSG mice. Twenty-four hours later with either (a) rituximab (b) NK-92-CD16-CD19 cells or (c) rituximab and NK-92-CD16-CD19 cells. Treatments are given to the mice every week for four months. It is contemplated that treatment with either NK-92-CD16-CD19 cells or a combination of rituximab and NK-92-CD16-CD19 cells significantly prolongs the life and extends survival of the mice compared to treatment with rituximab only.

Example 2: NK-92 Cells are Capable of expressing an Fc receptor and a CAR

Figure 1B:
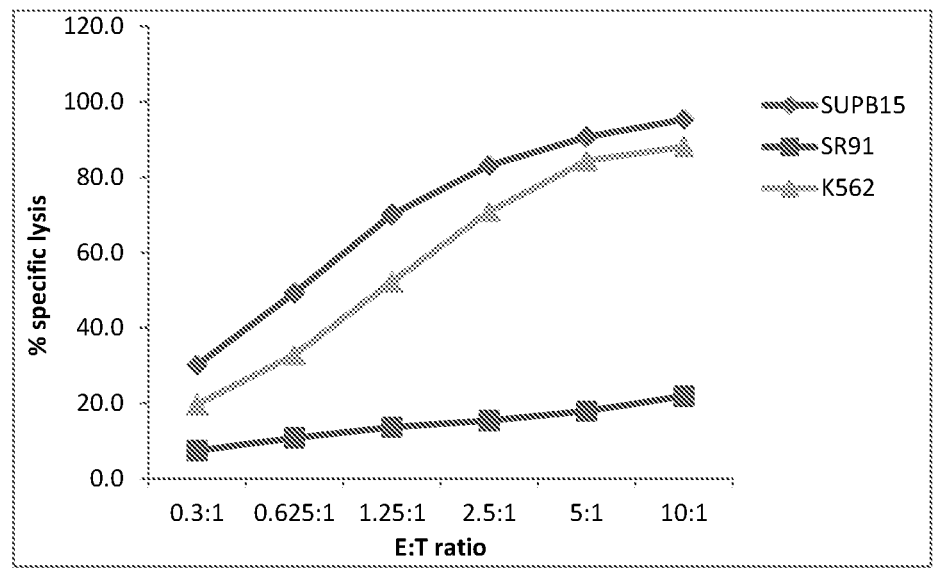
Figure 1C:
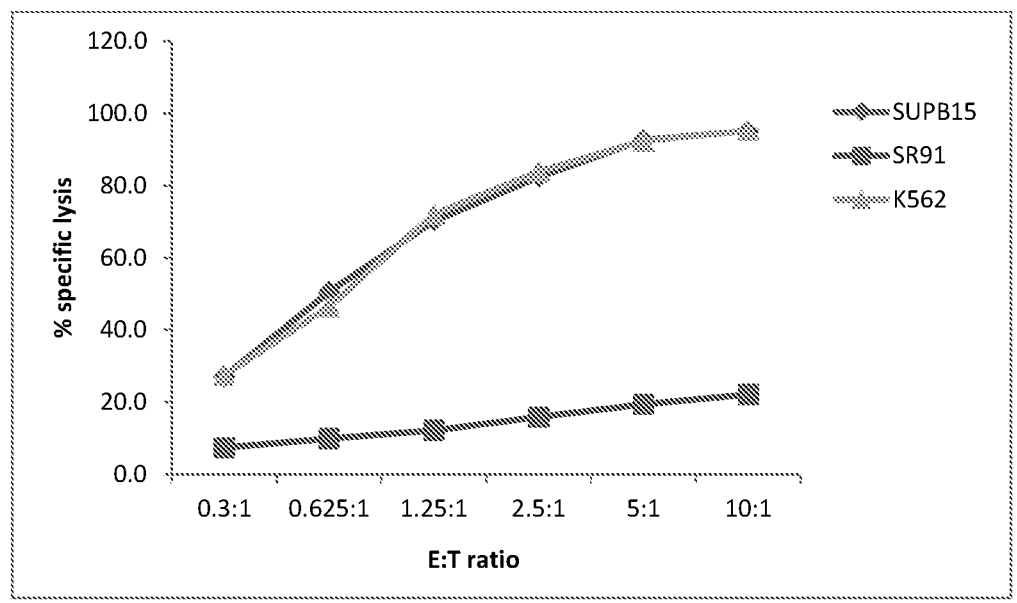

To analyze NK-92 cells expressing an Fc receptor and a CAR, in vitro cytotoxicity assays of NK-92 cells electroporated with mRNA coding for CD19-CAR against the cell lines K562 (NK-92 sensitive, CD19 negative), SUP-B15 (NK-92 resistant, CD19 positive), and SR-91 (NK-92 resistant, CD19 negative) were performed. The results are shown in FIGS. 1A, 1B and 1C. FIG. 1A shows killing of target cell lines by non-electroporated parental NK-92 cells. FIG. 1B shows killing of target cell lines by parental NK-92 cells expressing CD19-CAR. FIG. 1C shows killing of target cell lines by CD16(158V)-ERIL2 NK-92 cells expressing CD19-CAR. The NK-resistant, CD19 positive SUP-B15 cells become sensitive to CD19-CAR expressing NK-92 cells and CD16(158V)-ERIL2 NK-92 cells, while the NK-resistant, CD19 negative SR-91 cells remain resistant. Killing of K562 is unaffected by expression of CD19-CAR.

Example 3: Electroporation of mRNA for Chimeric Antigen Receptors (CARs) into Human NK Cell Lines Results in High Transfection Efficiency and Target Specific Cytotoxicity Data on mRNA transfection, expression and cytotoxicity of three different CARs: CD19, CD33 and CSPG-4 based on a first generation CAR construct is provided. Target cell lines for mRNA transfection were aNK (parental NK-92 cells) and haNK (high affinity FcR expressing NK-92). The scFv sequence was made to order by GeneArt (codon optimized) and mRNA was transfected with the MaxCyte GT to generate taNK (target-activated NK cell). Expression was determined by immune fluorescence using corresponding antibodies and cytotoxicity was measured using a standard flow cytometry assay.

After optimizing the transfection protocol with respect to voltage and time of electric pulse, it was determined that both aNK and haNK could effectively be transfected with all three mRNA CAR constructs. Viability of the transfected NK cells after transfection was consistently greater than 80% and expression of the corresponding CAR was 55-60% at 6 hours, 80-95% at 24 hours and greater than 80% at 48 hours. Specific cytotoxicity was determined against aNK resistant cell lines (SUP-B15 for CD19, SR-91 for CD33 and SK-MEL for CSPG-4). After transfection, cytotoxicity against aNK resistant cell lines at 24 hours was consistently greater than 80%.

Both aNK and haNK can be reliably and consistently transfected with mRNA for various CAR constructs maintaining high viability of the transfected NK cells, excellent expression of CAR as well as target cell specific cytotoxicity for at least 48 hours. This technology can easily be scaled up to clinical grade production of CAR expressing NK cells lines. The fact that haNK can be effectively transfected (to become t-haNK) opens the possibility of dual receptor non cross-reactive targeting (i.e., CD19 CAR with CD20 antibody) of malignancies.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

Illustrative Sequences

```
Low Affinity Immunoglobulin Gamma Fc Region Receptor III-A amino
acid sequence (mature form). The phenylalanine at position 158 is underlined
                                                                  SEQ ID NO: 1
Arg Thr Glu Asp Leu Pro Lys Ala Val Val Phe Leu Glu Pro Gln Trp Tyr Arg Val Leu Glu Lys Asp Ser Val Thr Leu Lys Cys Gln Gly Ala Tyr Ser Pro Glu Asp Asn Ser Thr Gln Trp Phe His Asn Glu Ser Leu Ile Ser Ser Gln Ala Ser Ser Tyr Phe Ile Asp Ala Ala Thr Val Asp Asp Ser Gly Glu Tyr Arg Cys Gln Thr Asn Leu Ser Thr Leu Ser Asp Pro Val Gln Leu Glu Val His Ile Gly Trp Leu Leu Leu Gln Ala Pro Arg Trp Val Phe Lys Glu Glu Asp Pro Ile His Leu Arg Cys His Ser Trp Lys Asn Thr Ala Leu His Lys Val Thr Tyr Leu Gln Asn Gly Lys Gly Arg Lys Tyr Phe His His Asn Ser Asp Phe Tyr Ile Pro Lys Ala Thr Leu Lys Asp Ser Gly Ser Tyr Phe Cys Arg Gly Leu Phe Gly Ser Lys Asn Val Ser Ser Glu Thr Val Asn Ile Thr Ile Thr Gln Gly Leu Ala Val Ser Thr Ile Ser Ser Phe Phe Pro Pro Gly Tyr Gln Val Ser Phe Cys Leu Val Met Val Leu Leu Phe Ala Val Asp Thr Gly Leu Tyr Phe Ser Val Lys Thr Asn Ile Arg Ser Ser Thr Arg Asp Trp Lys Asp His Lys Phe Lys Trp Arg Lys Asp Pro Gln Asp Lys High Affinity Variant F158V Immunoglobulin Gamma Fc Region
Receptor III-A amino acid sequence (mature form). The valine at position 158 is
underlined
                                                                  SEQ ID NO: 2
Arg Thr Glu Asp Leu Pro Lys Ala Val Val Phe Leu Glu Pro Gln Trp Tyr Arg Val Leu Glu Lys Asp Ser Val Thr Leu Lys Cys Gln Gly Ala Tyr Ser Pro Glu Asp Asn Ser Thr Gln Trp Phe His Asn Glu Ser Leu Ile Ser Ser Gln Ala Ser Ser Tyr Phe Ile Asp Ala Ala Thr Val Asp Asp Ser Gly Glu Tyr Arg Cys Gln Thr Asn Leu Ser Thr Leu Ser Asp Pro Val Gln Leu Glu Val His Ile Gly Trp Leu Leu Leu Gln Ala Pro Arg Trp Val Phe Lys Glu Glu Asp Pro Ile His Leu Arg Cys His Ser Trp Lys Asn Thr Ala Leu His Lys Val Thr Tyr Leu Gln Asn Gly Lys Gly Arg Lys Tyr Phe His His Asn Ser Asp Phe Tyr Ile Pro Lys Ala Thr Leu Lys Asp Ser Gly Ser Tyr Phe Cys Arg Gly Leu Val Gly Ser Lys Asn Val Ser Ser Glu Thr Val Asn Ile Thr Ile Thr Gln Gly Leu Ala Val Ser Thr Ile Ser Ser Phe Phe Pro Pro Gly Tyr Gln Val Ser Phe Cys Leu Val Met Val Leu Leu Phe Ala Val Asp Thr Gly Leu Tyr Phe Ser Val Lys Thr Asn Ile Arg Ser Ser Thr Arg Asp Trp Lys Asp His Lys Phe Lys Trp Arg Lys Asp Pro Gln Asp Lys
```

-continued

Low Affinity Immunoglobulin Gamma Fc Region Receptor III-A amino acid sequence (precursor form). Position 176 of the precursor form corresponds to position 158 of the mature form. The Phe at position 176 is underlined.

SEQ ID NO: 3

Met Trp Gln Leu Leu Pro Thr Ala Leu Leu Leu Leu Val Ser Ala Gly Met Arg Thr Glu

Asp Leu Pro Lys Ala Val Val Phe Leu Glu Pro Gln Trp Tyr Arg Val Leu Glu Lys Asp Ser

Val Thr Leu Lys Cys Gln Gly Ala Tyr Ser Pro Glu Asp Asn Ser Thr Gln Trp Phe His Asn

Glu Ser Leu Ile Ser Ser Gln Ala Ser Ser Tyr Phe Ile Asp Ala Ala Thr Val Asp Asp Ser Gly

Glu Tyr Arg Cys Gln Thr Asn Leu Ser Thr Leu Ser Asp Pro Val Gln Leu Glu Val His Ile Gly

Trp Leu Leu Leu Gln Ala Pro Arg Trp Val Phe Lys Glu Glu Asp Pro Ile His Leu Arg Cys

His Ser Trp Lys Asn Thr Ala Leu His Lys Val Thr Tyr Leu Gln Asn Gly Lys Gly Arg Lys

Tyr Phe His His Asn Ser Asp Phe Tyr Ile Pro Lys Ala Thr Leu Lys Asp Ser Gly Ser Tyr Phe

Cys Arg Gly Leu Phe Gly Ser Lys Asn Val Ser Ser Glu Thr Val Asn Ile Thr Ile Thr Gln Gly

Leu Ala Val Ser Thr Ile Ser Ser Phe Phe Pro Pro Gly Tyr Gln Val Ser Phe Cys Leu Val Met

Val Leu Leu Phe Ala Val Asp Thr Gly Leu Tyr Phe Ser Val Lys Thr Asn Ile Arg Ser Ser Thr

Arg Asp Trp Lys Asp His Lys Phe Lys Trp Arg Lys Asp Pro Gln Asp Lys

High Affinity Variant Immunoglobulin Gamma Fc Region Receptor III-A amino acid sequence (precursor form). Position 176 of the precursor form corresponds to positions 158 of the mature form. The Val at position 176 is underlined.

SEQ ID NO: 4

Met Trp Gln Leu Leu Leu Pro Thr Ala Leu Leu Leu Leu Val Ser Ala Gly Met Arg Thr Glu

Asp Leu Pro Lys Ala Val Val Phe Leu Glu Pro Gln Trp Tyr Arg Val Leu Glu Lys Asp Ser

Val Thr Leu Lys Cys Gln Gly Ala Tyr Ser Pro Glu Asp Asn Ser Thr Gln Trp Phe His Asn

Glu Ser Leu Ile Ser Ser Gln Ala Ser Ser Tyr Phe Ile Asp Ala Ala Thr Val Asp Asp Ser Gly

Glu Tyr Arg Cys Gln Thr Asn Leu Ser Thr Leu Ser Asp Pro Val Gln Leu Glu Val His Ile Gly

Trp Leu Leu Leu Gln Ala Pro Arg Trp Val Phe Lys Glu Glu Asp Pro Ile His Leu Arg Cys

His Ser Trp Lys Asn Thr Ala Leu His Lys Val Thr Tyr Leu Gln Asn Gly Lys Gly Arg Lys

Tyr Phe His His Asn Ser Asp Phe Tyr Ile Pro Lys Ala Thr Leu Lys Asp Ser Gly Ser Tyr Phe

Cys Arg Gly Leu Val Gly Ser Lys Asn Val Ser Ser Glu Thr Val Asn Ile Thr Ile Thr Gln Gly

Leu Ala Val Ser Thr Ile Ser Ser Phe Phe Pro Pro Gly Tyr Gln Val Ser Phe Cys Leu Val Met

Val Leu Leu Phe Ala Val Asp Thr Gly Leu Tyr Phe Ser Val Lys Thr Asn Ile Arg Ser Ser Thr

Arg Asp Trp Lys Asp His Lys Phe Lys Trp Arg Lys Asp Pro Gln Asp Lys

Polynucleotide Encoding the Low Affinity Immunoglobulin Gamma Fc Region Receptor III-A (Precursor) (Encodes phenylalanine at position 158)

SEQ ID NO: 5 atgtggcagc tgctcctccc aactgctctg ctacttctag tttcagctgg catgcggact gaagatctcc caaaggctgt ggtgttcctg agcctcaat ggtacagggt gctcgagaag acagtgtga ctctgaagtc cagggagcc tactcccctg aggacaattc cacacagtgg tttcacaatg agagcctcat ctcaagccag gcctcgagct acttcattga cgctgccaca gtcgacgaca gtggagagta caggtgccag acaaacctct ccaccctcag tgacccggta cagctagaag tccatatcgg ctggctgttg ctccaggccc ctcggtgggt gttcaaggag aagaccccta ttcacctgag gtgtcacagc tggaagaaca ctgctctgca taaggtcaca tatttacaga atggcaaagg caggaagtat tttcatcata attctgactt ctacattcca aaagccacac tcaaagacag cggctcctac ttctgcaggg ggcttttttgg gagtaaaaat gtgtcttcag agactgtgaa catcaccatc actcaaggtt tggcagtgtc aaccatctca tcattctttc cacctgggta ccaagtctct ttctgcttgg tgatggtact cctttttgca gtggacacag gactatattt ctctgtgaag acaaacattc gaagctcaac aagagactgg aaggaccata aatttaaatg gagaaaggac cctcaagaca atga Wild-Type IL-2
SEQ ID NO: 6

Met Tyr Arg Met Gln Leu Leu Ser Cys Ile Ala Leu Ser Leu Ala Leu Val Thr Asn Ser Ala Pro
Thr Ser Ser Ser Thr Lys Lys Thr Gln Leu Gln Leu Glu His Leu Leu Leu Asp Leu Gln Met Ile
Leu Asn Gly Ile Asn Asn Tyr Lys Asn Pro Lys Leu Thr Arg Met Leu Thr Phe Lys Phe Tyr
Met Pro Lys Lys Ala Thr Glu Leu Lys His Leu Gln Cys Leu Glu Glu Glu Leu Lys Pro Leu
Glu Glu Val Leu Asn Leu Ala Gln Ser Lys Asn Phe His Leu Arg Pro Arg Asp Leu Ile Ser
Asn Ile Asn Val Ile Val Leu Glu Leu Lys Gly Ser Glu Thr Thr Phe Met Cys Glu Tyr Ala Asp
Glu Thr Ala Thr Ile Val Glu Phe Leu Asn Arg Trp Ile Thr Phe Cys Gln Ser Ile Ile Ser Thr
Leu Thr

IL-2-ER
SEQ ID NO: 7

Met Tyr Arg Met Gln Leu Leu Ser Cys Ile Ala Leu Ser Leu Ala Leu Val Thr Asn Ser Ala Pro
Thr Ser Ser Ser Thr Lys Lys Thr Gln Leu Gln Leu Glu His Leu Leu Leu Asp Leu Gln Met Ile
Leu Asn Gly Ile Asn Asn Tyr Lys Asn Pro Lys Leu Thr Arg Met Leu Thr Phe Lys Phe Tyr
Met Pro Lys Lys Ala Thr Glu Leu Lys His Leu Gln Cys Leu Glu Glu Glu Leu Lys Pro Leu
Glu Glu Val Leu Asn Leu Ala Gln Ser Lys Asn Phe His Leu Arg Pro Arg Asp Leu Ile Ser
Asn Ile Asn Val Ile Val Leu Glu Leu Lys Gly Ser Glu Thr Thr Phe Met Cys Glu Tyr Ala Asp
Glu Thr Ala Thr Ile Val Glu Phe Leu Asn Arg Trp Ile Thr Phe Cys Gln Ser Ile Ile Ser Thr
Leu Thr Gly Ser Glu Lys Asp Glu Leu

CD19-CAR DNA sequence
SEQ ID NO: 8

CCCGGGAATT CGCCACCATG GACTGGATCT GGCGGATCCT GTTCCTCGTG
GGAGCCGCCA CAGGCGCCCA TTCTGCCCAG CCCGCCGACA TCCAGATGAC
CCAGACCACC AGCAGCCTGA GCGCCAGCCT GGGCGACAGA GTGACCATCA
GCTGCCGGGC CAGCCAGGAC ATCAGCAAGT ACCTGAACTG GTATCAGCAG
AAACCCGACG GCACCGTGAA GCTGCTGATC TACCACACCA GCCGGCTGCA
CAGCGGCGTG CCCAGCAGAT TTTCTGGCAG CGGCAGCGGC ACCGACTACA
GCCTGACCAT CTCCAACCTG GAACAGGAAG ATATCGCTAC CTACTTCTGT
CAGCAAGGCA ACACCCTGCC CTACACCTTC GGCGGAGGCA CCAAGCTGGA
ACTGAAGAGA GGCGGCGGAG GCTCTGGTGG AGGCGGATCT GGGGGCGGAG
GAAGTGGCGG GGGAGGATCT GAAGTGCAGC TGCAGCAGAG CGGCCCTGGC
CTGGTGGCCC CTAGCCAGAG CCTGTCCGTG ACCTGTACCG TGTCCGGCGT
GTCCCTGCCC GACTACGGCG TGTCCTGGAT CCGGCAGCCC CCCAGAAAGG
GCCTGGAATG GCTGGGCGTG ATCTGGGGCA GCGAGACAAC CTACTACAAC
AGCGCCCTGA AGTCCCGGCT GACCATCATC AAGGACAACA GCAAGAGCCA
GGTGTTCCTG AAGATGAACA GCCTGCAGAC CGACGACACC GCCATCTACT
ACTGCGCCAA GCACTACTAC TACGGCGGCA GCTACGCCAT GGACTACTGG
GGCCAGGGCA CCACCGTGAC CGTGTCCAGC GCCCTGTCCA ACAGCATCAT
GTACTTCAGC CACTTCGTGC CCGTGTTTCT GCCCGCCAAG CCCACCACCA
CCCCTGCCCC TAGACCTCCC ACCCCAGCCC CAACAATCGC CAGCCAGCCT
CTGTCCCTGC GGCCCGAAGC TAGCAGACCT GCTGCCGGCG GAGCCGTGCA
CACCAGAGGC CTGGACCCCA AGCTGTGCTA CCTGCTGGAC GGCATCCTGT
TCATCTATGG CGTGATCCTG ACCGCCCTGT TCCTGAGAGT GAAGTTCAGC

-continued

```
AGAAGCGCCG ACGCCCCTGC CTACCAGCAG GGCCAGAACC AGCTGTACAA
CGAGCTGAAC CTGGGCAGAC GGGAAGAGTA CGACGTGCTG GACAAGCGGA
GAGGCAGGGA CCCCGAGATG GGCGGCAAGC CCAGACGGAA GAACCCCCAG
GAAGGCCTGT ATAACGAACT GCAGAAAGAC AAGATGGCCG AGGCCTACAG
CGAGATCGGC ATGAAGGGCG AGCGGCGGAG GGGCAAGGGC CACGATGGAC
TGTACCAGGG CCTGAGCACC GCCACCAAGG ACACCTACGA CGCCCTGCAC
ATGCAGGCCC TGCCCCCCAG ATGACAGCCA GGGCATTTCT CCCTCGAGCG
GCCGC
```

CD19-CAR amino acids sequence  SEQ ID NO: 9

```
MDWIWRILFL VGAATGAHSA QPADIQMTQT TSSLSASLGD RVTISCRASQ
DISKYLNWYQ QKPDGTVKLL IYHTSRLHSG VPSRFSGSGS GTDYSLTISN
LEQEDIATYF CQQGNTLPYT FGGGTKLELK RGGGGSGGGG SGGGGSGGGG
SEVQLQQSGP GLVAPSQSLS VTCTVSGVSL PDYGVSWIRQ PPRKGLEWLG
VIWGSETTYY NSALKSRLTI IKDNSKSQVF LKMNSLQTDD TAIYYCAKHY
YYGGSYAMDY WGQGTTVTVS SALSNSIMYF SHFVPVFLPA KPTTTPAPRP
PTPAPTIASQ PLSLRPEASR PAAGGAVHTR GLDPKLCYLL DGILFIYGVI
LTALFLRVKF SRSADAPAYQ QGQNQLYNEL NLGRREEYDV LDKRRGRDPE
MGGKPRRKNP QEGLYNELQK DKMAEAYSEI GMKGERRRGK GHDGLYQGLS
TATKDTYDAL HMQALPPR
```

CD33-CAR DNA sequence  SEQ ID NO: 10

```
CCCGGGAATT CGCCACCATG GACTGGATCT GGCGGATCCT GTTCCTCGTG
GGAGCCGCCA CAGGCGCCCA TTCTGCCCAG CCCGCCGACA TCCAGATGAC
CCAGAGCCCT AGCAGCCTGA GCGCCAGCGT GGGCGACAGA GTGACCATCA
CCTGTCGGGC CAGCGAGAGC GTGGACAACT ACGGCATCAG CTTCATGAAC
TGGTTCCAGC AGAAGCCCGG CAAGGCCCCC AAGCTGCTGA TCTACGCCGC
CAGCAATCAG GGCAGCGGCG TGCCCAGCAG ATTCAGCGGC TCTGGCAGCG
GCACCGACTT CACCCTGACC ATCAGCAGCC TGCAGCCCGA CGACTTCGCC
ACCTACTACT GCCAGCAGAG CAAAGAGGTG CCCTGGACCT TCGGCCAGGG
CACCAAGGTG GAAATCAAGG GCGGAGGCGG CAGCGGAGGT GGAGGAAGTG
GCGGCGAGG ATCTCAGGTG CAGCTGGTGC AGTCTGGCGC CGAAGTGAAG
AAACCCGGCA GCAGCGTGAA GGTGTCCTGC AAGGCCAGCG GCTACACCTT
CACCGACTAC AACATGCACT GGGTCCGCCA GGCCCCAGGC CAGGGACTGG
AATGGATCGG CTACATCTAC CCCTACAACG GCGGCACCGG CTACAACCAG
AAGTTCAAGA GCAAGGCCAC CATCACCGCC GACGAGAGCA CCAACACCGC
CTACATGGAA CTGAGCAGCC TGCGGAGCGA GGACACCGCC GTGTACTACT
GCGCCAGAGG CAGACCCGCC ATGGACTACT GGGGCCAGGG AACCCTGGTG
ACAGTGTCCA GCGCCCTGAG CAACAGCATC ATGTACTTCA GCCACTTCGT
GCCCGTGTTT CTGCCCGCCA AGCCCACCAC CACCCCTGCC CCTAGACCTC
CCACCCCAGC CCCAACAATC GCCAGCCAGC CTCTGTCCCT GCGGCCCGAA
GCTAGCAGAC CTGCTGCCGG CGGAGCCGTG CACACCAGAG GCCTGGACCC
```

-continued

```
CAAGCTGTGC TACCTGCTGG ACGGCATCCT GTTCATCTAC GGCGTGATCC
TGACCGCCCT GTTCCTGAGA GTGAAGTTCA GCAGAAGCGC CGACGCCCCT
GCCTACCAGC AGGGCCAGAA CCAGCTGTAC AACGAGCTGA ACCTGGGCAG
ACGGGAAGAG TACGACGTGC TGGACAAGCG GAGAGGCAGG GACCCCGAGA
TGGGCGGCAA GCCCAGACGG AAGAACCCCC AGGAAGGCCT GTATAACGAA
CTGCAGAAAG ACAAGATGGC CGAGGCCTAC AGCGAGATCG GCATGAAGGG
CGAGCGGCGG AGGGGCAAGG GCCACGATGG ACTGTACCAG GGCCTGAGCA
CCGCCACCAA GGACACCTAC GACGCCCTGC ACATGCAGGC CCTGCCCCCC
AGATGACAGC CAGGGCATTT CTCCCTCGAG CGGCCGC
```

CD33-CAR amino acids sequence    SEQ ID NO: 11

```
MDWIWRILFL VGAATGAHSA QPADIQMTQS PSSLSASVGD RVTITCRASE
SVDNYGISFM NWFQQKPGKA PKLLIYAASN QGSGVPSRFS GSGSGTDFTL
TISSLQPDDF ATYYCQQSKE VPWTFGQGTK VEIKGGGGSG GGGSGGGGSQ
VQLVQSGAEV KKPGSSVKVS CKASGYTFTD YNMHWVRQAP GQGLEWIGYI
YPYNGGTGYN QKFKSKATIT ADESTNTAYM ELSSLRSEDT AVYYCARGRP
AMDYWGQGTL VTVSSALSNS IMYFSHFVPV FLPAKPTTTP APRPPTPAPT
IASQPLSLRP EASRPAAGGA VHTRGLDPKL CYLLDGILFI YGVILTALFL
RVKFSRSADA PAYQQGQNQL YNELNLGRRE EYDVLDKRRG RDPEMGGKPR
RKNPQEGLYN ELQKDKMAEA YSEIGMKGER RRGKGHDGLY QGLSTATKDT
YDALHMQALP PR
```

CSPG4-CAR DNA sequence    SEQ ID NO: 12

```
CCCGGGAATT CGCCACCATG GACTGGATCT GGCGCATCCT CTTCCTCGTC
GGCGCTGCTA CCGGCGCTCA TTCGGCCCAG CCGGCCGATA TCGAGCTCAC
CCAATCTCCA AAATTCATGT CCACATCAGT AGGAGACAGG GTCAGCGTCA
CCTGCAAGGC CAGTCAGAAT GTGGATACTA ATGTAGCGTG GTATCAACAA
AAACCAGGGC AATCTCCTGA ACCACTGCTT TTCTCGGCAT CCTACCGTTA
CACTGGAGTC CCTGATCGCT TCACAGGCAG TGGATCTGGG ACAGATTTCA
CTCTCACCAT CAGCAATGTG CAGTCTGAAG ACTTGGCAGA GTATTTCTGT
CAGCAATATA ACAGCTATCC TCTGACGTTC GGTGGCGGCA CCAAGCTGGA
AATCAAACGG GCTGCCGCAG AAGGTGGAGG CGGTTCAGGT GGCGGAGGTT
CCGGCGGAGG TGGCTCTGGC GGTGGCGGAT CGGCCATGGC CCAGGTGAAG
CTGCAGCAGT CAGGAGGGGG CTTGGTGCAA CCTGGAGGAT CCATGAAACT
CTCCTGTGTT GTCTCTGGAT TCACTTTCAG TAATTACTGG ATGAACTGGG
TCCGCCAGTC TCCAGAGAAG GGGCTTGAGT GGATTGCAGA AATTAGATTG
AAATCCAATA ATTTTGGAAG ATATTATGCG GAGTCTGTGA AGGGGAGGTT
CACCATCTCA AGAGATGATT CCAAAAGTAG TGCCTACCTG CAAATGATCA
ACCTAAGAGC TGAAGATACT GGCATTTATT ACTGTACCAG TTATGGTAAC
TACGTTGGGC ACTATTTTGA CCACTGGGGC CAAGGGACCA CGGTCACCGT
ATCGAGTGCC GCGGTTCTAG AGCTCTTGAG CAACTCCATC ATGTACTTCA
GCCACTTCGT GCCGGTCTTC CTGCCAGCGA AGCCCACCAC GACGCCAGCG
CCGCGACCAC CAACACCGGC GCCCACCATC GCGTCGCAGC CCCTGTCCCT
```

```
                                                          -continued
GCGCCCAGAG GCGTGCCGGC CAGCGGCGGG GGGCGCAGTG CACACGAGGG

GGCTGGACCT GCTGGATCCC AAACTCTGCT ACCTGCTGGA TGGAATCCTC

TTCATCTATG GTGTCATTCT CACTGCCTTG TTCCTGAGAG TGAAGTTCAG

CAGGAGCGCA GACGCCCCCG CGTACCAGCA GGGCCAGAAC CAGCTCTATA

ACGAGCTCAA TCTAGGACGA AGAGAGGAGT ACGATGTTTT GGACAAGAGA

CGTGGCCGGG ACCCTGAGAT GGGGGGAAAG CCGCAGAGAA GGAAGAACCC

TCAGGAAGGC CTGTACAATG AACTGCAGAA AGATAAGATG GCGGAGGCCT

ACAGTGAGAT TGGGATGAAA GGCGAGCGCC GGAGGGGCAA GGGGCACGAT

GGCCTTTACC AGGGTCTCAG TACAGCCACC AAGGACACCT ACGACGCCCT

TCACATGCAG GCCCTGCCCC CTCGCTAACA GCCAGGGCAT TTCTCCCTCG

AGCGGCCGC
```

CSPG4-CAR amino acid sequence          SEQ ID NO. 13

```
MDWIWRILFL VGAATGAHSA QPADIELTQS PKFMSTSVGD RVSVTCKASQ

NVDTNVAWYQ QKPGQSPEPL LFSASYRYTG VPDRFTGSGS GTDFTLTISN

VQSEDLAEYF CQQYNSYPLT FGGGTKLEIK RAAAEGGGGS GGGGSGGGGS

GGGGSAMAQV KLQQSGGGLV QPGGSMKLSC VVSGFTFSNY WMNWVRQSPE

KGLEWIAEIR LKSNNFGRYY AESVKGRFTI SRDDSKSSAY LQMINLRAED

TGIYYCTSYG NYVGHYFDHW GQGTTVTVSS AAVLELLSNS IMYFSHFVPV

FLPAKPTTTP APRPPTPAPT IASQPLSLRP EACRPAAGGA VHTRGLDLLD

PKLCYLLDGI LFIYGVILTA LFLRVKFSRS ADAPAYQQGQ NQLYNELNLG

RREEYDVLDK RRGRDPEMGG KPQRRKNPQE GLYNELQKDK MAEAYSEIGM

KGERRRGKGH DGLYQGLSTA TKDTYDALHM QALPPR
```

---

What is claimed is:

1. A method of treating a B-cell malignancy in a patient in need thereof, the method comprising administering to the patient an effective amount of an NK-92 cell line comprising modified NK-92 cells, wherein the modified NK-92 cells are modified to each express at least one Fc receptor and at least one chimeric antigen receptor (CAR), such that the at least one Fc receptor and the at least one CAR are displayed on the cell surface of the modified NK-92 cells, wherein the CAR comprises the amino acid sequence as defined in SEQ ID NO:9.

2. The method of claim 1, wherein the Fc receptor is FcγRIII-A (CD16) or a CD16 polypeptide having a valine at position 158 of the mature form of the CD16.

3. The method of claim 1, wherein the Fc receptor comprises an amino acid sequence having at least 90% sequence identity to SEQ ID NO:2 and comprises valine at position 158.

4. The method of claim 1, wherein the Fc receptor comprises the amino acid sequence of SEQ ID NO:2.

5. The method of claim 1, wherein the CAR targets the CD19 tumor-associated antigen.

6. The method of claim 1, wherein the modified NK-92 cells are further modified to express a cytokine.

7. The method of claim 6, wherein the cytokine is interleukin-2 or a variant thereof and/or interleukin-15 or a variant thereof.

8. The method of claim 7, wherein the cytokine is targeted to the endoplasmic reticulum.

9. The method of claim 1, wherein the Fc receptor and the CAR are encoded on different vectors.

10. The method of claim 1, wherein the modified NK-92 cells have undergone less than 10 population doublings.

11. The method of claim 1, wherein the modified NK-92 cells are administered to the patient by a route selected from the group consisting of intravenous, intraperitoneal, and subcutaneous.

12. The method of claim 1, wherein the B-cell malignancy is selected from the group consisting of a leukemia, chronic B-cell leukemia, acute lymphoblastic leukemia (ALL), chronic lymphocytic leukemia (CLL), ALL post hematopoietic stem cell transplantation (HSCT), a lymphoma, Waldenstrom's macroglobulinemia, heavy chain disease, non-Hodgkin's lymphoma (NHL), refractory follicular lymphoma; B-cell non-Hodgkin lymphoma (B-NHL), B-cell malignancies post-HSCT, and B-lineage lymphoid malignancies post umbilical cord blood transplantation (UCBT).

13. The method of claim 1, wherein about $1 \times 10^8$ to about $1 \times 10^{11}$ modified NK-92 cells per $m^2$ of body surface area of the patient are administered to the patient.

14. The method of claim 1, further comprising administering to the patient an effective amount of at least one monoclonal antibody.

15. The method of claim 14, wherein the monoclonal antibody is a naked monoclonal antibody, a conjugated monoclonal antibody or a bispecific monoclonal antibody.

16. The method of claim 14, wherein the monoclonal antibody is selected from the group consisting of alemtuzumab, rituxumab, trastuzumab, ibritumomab, brentuximab, gemtuzumab, adotranstuzumab, blinatunomab, avelumamab, daratumumab and elotuzumab.

17. The method of claim 14, wherein the monoclonal antibody and the modified NK-92 cells are administered concurrently to the patient.

18. The method of claim 1, further comprising administering stem cell transplantation to the patient.

19. A method of treating a B-cell malignancy in a patient in need thereof, the method comprising administering to the patient an effective amount of an NK-92 cell line comprising modified NK-92 cells,
wherein the modified NK-92 cells are modified to each express at least one Fc receptor and at least one chimeric antigen receptor (CAR), such that the at least one Fc receptor and the at least one CAR are displayed on the cell surface of the modified NK-92 cells, and
wherein the CAR comprises an antibody comprising the amino acid sequences of the six CDRs of SEQ ID NO:9.

20. The method of claim 19, wherein the Fc receptor is FcγRIII-A (CD16) or a CD16 polypeptide having a valine at position 158 of the mature form of the CD16.

* * * * *

SEQUENCE LISTING

<160> NUMBER OF SEQ ID NOS: 13

<210> SEQ ID NO 1
<211> LENGTH: 236
<212> TYPE: PRT
<213> ORGANISM: Artificial Sequence
<220> FEATURE:
<223> OTHER INFORMATION: synthetic Low Affinity Immunoglobulin Gamma Fc
      Region Receptor III-A amino acid sequence (mature form)

<400> SEQUENCE: 1

```
Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asp
    50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95
```

```
Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
            115                 120                 125

Gly Arg Lys Tyr Phe His His Asn Ser Asp Phe Tyr Ile Pro Lys Ala
        130                 135                 140

Thr Leu Lys Asp Ser Gly Ser Tyr Phe Cys Arg Gly Leu Phe Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Phe Pro Pro Gly Tyr Gln Val Ser
            180                 185                 190

Phe Cys Leu Val Met Val Leu Leu Phe Ala Val Asp Thr Gly Leu Tyr
            195                 200                 205

Phe Ser Val Lys Thr Asn Ile Arg Ser Ser Thr Arg Asp Trp Lys Asp
        210                 215                 220

His Lys Phe Lys Trp Arg Lys Asp Pro Gln Asp Lys
225                 230                 235

<210> SEQ ID NO 2
<211> LENGTH: 236
<212> TYPE: PRT
<213> ORGANISM: Artificial Sequence
<220> FEATURE:
<223> OTHER INFORMATION: synthetic High Affinity Variant F158V
      Immunoglobulin Gamma Fc Region Receptor III-A amino acid sequence
      (mature form)

<400> SEQUENCE: 2

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
            20                  25                  30

Tyr Ser Pro Glu Asp Asn Ser Thr Gln Trp Phe His Asn Glu Ser Leu
        35                  40                  45

Ile Ser Ser Gln Ala Ser Ser Tyr Phe Ile Asp Ala Ala Thr Val Asp
50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
            115                 120                 125

Gly Arg Lys Tyr Phe His His Asn Ser Asp Phe Tyr Ile Pro Lys Ala
        130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly Leu
                165                 170                 175

Ala Val Ser Thr Ile Ser Ser Phe Phe Pro Pro Gly Tyr Gln Val Ser
            180                 185                 190

Phe Cys Leu Val Met Val Leu Leu Phe Ala Val Asp Thr Gly Leu Tyr
            195                 200                 205

Phe Ser Val Lys Thr Asn Ile Arg Ser Ser Thr Arg Asp Trp Lys Asp
```

```
                210                 215                 220
His Lys Phe Lys Trp Arg Lys Asp Pro Gln Asp Lys
225                 230                 235

<210> SEQ ID NO 3
<211> LENGTH: 254
<212> TYPE: PRT
<213> ORGANISM: Artificial Sequence
<220> FEATURE:
<223> OTHER INFORMATION: synthetic Low Affinity Immunoglobulin Gamma Fc
      Region Receptor III-A amino acid sequence (precursor form)

<400> SEQUENCE: 3

Met Trp Gln Leu Leu Pro Thr Ala Leu Leu Leu Leu Val Ser Ala
1               5                   10                  15

Gly Met Arg Thr Glu Asp Leu Pro Lys Ala Val Val Phe Leu Glu Pro
                20                  25                  30

Gln Trp Tyr Arg Val Leu Glu Lys Asp Ser Val Thr Leu Lys Cys Gln
            35                  40                  45

Gly Ala Tyr Ser Pro Glu Asp Asn Ser Thr Gln Trp Phe His Asn Glu
        50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Phe
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 4
<211> LENGTH: 254
<212> TYPE: PRT
<213> ORGANISM: Artificial Sequence
<220> FEATURE:
<223> OTHER INFORMATION: synthetic High Affinity Variant Immunoglobulin
      Gamma Fc Region Receptor III-A amino acid sequence (precursor
      form)

<400> SEQUENCE: 4

Met Trp Gln Leu Leu Pro Thr Ala Leu Leu Leu Leu Val Ser Ala
1               5                   10                  15
```

```
Gly Met Arg Thr Glu Asp Leu Pro Lys Ala Val Val Phe Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

```
<210> SEQ ID NO 5
<211> LENGTH: 765
<212> TYPE: DNA
<213> ORGANISM: Artificial Sequence
<220> FEATURE:
<223> OTHER INFORMATION: synthetic Polynucleotide Encoding the Low
      Affinity Immunoglobulin Gamma Fc Region Receptor III-A (Precursor)

<400> SEQUENCE: 5
atgtggcagc tgctcctccc aactgctctg ctacttctag tttcagctgg catgcggact      60
gaagatctcc caaaggctgt ggtgttcctg gagcctcaat ggtacagggt gctcgagaag    120
gacagtgtga ctctgaagtg ccaggggagcc tactcccctg aggacaattc acacagtgg    180 tttcacaatg agagcctcat ctcaagccag gcctcgagct acttcattga cgctgccaca    240
gtcgacgaca gtggagagta caggtgccag acaaacctct ccaccctcag tgacccggtg    300
cagctagaag tccatatcgg ctggctgttg ctccaggccc ctcggtgggt gttcaaggag    360
gaagacccta ttcacctgag gtgtcacagc tggaagaaca ctgctctgca taaggtcaca    420
tatttacaga atggcaaagg caggaagtat tttcatcata attctgactt ctacattcca    480
aaagccacac tcaaagacag cggctcctac ttctgcaggg ggcttttgg gagtaaaaat    540 gtgtcttcag agactgtgaa catcaccatc actcaaggtt tggcagtgtc aaccatctca    600
tcattctttc cacctgggta ccaagtctct ttctgcttgg tgatggtact ccttttttgca    660 gtggacacag gactatattt ctctgtgaag acaaacattc gaagctcaac aagagactgg    720
```
aaggaccata aatttaaatg gagaaaggac cctcaagaca aatga 765

<210> SEQ ID NO 6
<211> LENGTH: 153
<212> TYPE: PRT
<213> ORGANISM: Artificial Sequence
<220> FEATURE:
<223> OTHER INFORMATION: synthetic polypeptide - Wild-Type IL-2

<400> SEQUENCE: 6

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 7
<211> LENGTH: 160
<212> TYPE: PRT
<213> ORGANISM: Artificial Sequence
<220> FEATURE:
<223> OTHER INFORMATION: synthetic polypeptide IL-2-ER

<400> SEQUENCE: 7

```
Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140
```

Cys Gln Ser Ile Ile Ser Thr Leu Thr Gly Ser Glu Lys Asp Glu Leu
145                 150                 155                 160

<210> SEQ ID NO 8
<211> LENGTH: 1455
<212> TYPE: DNA
<213> ORGANISM: Artificial Sequence
<220> FEATURE:
<223> OTHER INFORMATION: synthetic CD19-CAR DNA sequence

<400> SEQUENCE: 8

```
cccgggaatt cgccaccatg gactggatct ggcggatcct gttcctcgtg ggagccgcca      60
caggcgccca ttctgcccag cccgccgaca tccagatgac ccagaccacc agcagcctga     120
gcgccagcct gggcgacaga gtgaccatca gctgccgggc cagccaggac atcagcaagt     180
acctgaactg gtatcagcag aaacccgacg gcaccgtgaa gctgctgatc taccacacca     240
gccggctgca cagcggcgtg cccagcgat tttctggcag cggcagcggc accgactaca     300
gcctgaccat ctccaacctg aacaggaag atatcgctac ctacttctgt cagcaaggca     360
acacccctgcc ctacaccttc ggcggaggca ccaagctgga actgaagaga ggcggcggag     420
gctctggtgg aggcggatct ggggcgag gaagtggcgg gggaggatct gaagtgcagc     480
tgcagcagag cggccctggc ctggtggccc ctagccagag cctgtccgtg acctgtaccg     540
tgtccggcgt gtccctgccc gactacggcg tgtcctggat ccggcagccc cccagaaagg     600
gcctggaatg gctgggcgtg atctggggca gcgagacaac ctactacaac agcgccctga     660
agtcccggct gaccatcatc aaggacaaca gcaagagcca ggtgttcctg aagatgaaca     720
gcctgcagac cgacgacacc gccatctact actgcgccaa gcactactac tacggcggca     780
gctacgccat ggactactgg ggccagggca ccaccgtgac cgtgtccagc gccctgtcca     840
acagcatcat gtacttcagc cacttcgtgc ccgtgtttct gcccgccaag cccaccacca     900
cccctgcccc tagacctccc accccagccc aacaatcgc cagccagcct ctgtccctgc     960
ggcccgaagc tagcagacct gctgccggcg gagccgtgca caccagaggc ctggacccca    1020
agctgtgcta cctgctggac ggcatcctgt tcatctatgg cgtgatcctg accgccctgt    1080
tcctgagagt gaagttcagc agaagcgccg acgcccctgc ctaccagcag ggccagaacc    1140
agctgtacaa cgagctgaac ctgggcagac gggaagagta cgacgtgctg gacaagcgga    1200
gaggcaggga ccccgagatg ggcggcaagc ccagacggaa gaacccccag gaaggcctgt    1260
ataacgaact gcagaaagac aagatggccg aggcctacag cgagatcggc atgaagggcg    1320
agcggcggag gggcaagggc cacgatggac tgtaccaggg cctgagcacc gccaccaagg    1380
acacctacga cgccctgcac atgcaggccc tgccccccag atgacagcca gggcatttct    1440
ccctcgagcg gccgc                                                     1455
```

<210> SEQ ID NO 9
<211> LENGTH: 468
<212> TYPE: PRT
<213> ORGANISM: Artificial Sequence
<220> FEATURE:
<223> OTHER INFORMATION: synthetic CD19-CAR amino acids sequence

<400> SEQUENCE: 9

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Thr Thr Ser
                20                  25                  30

```
Ser Leu Ser Ala Ser Leu Gly Asp Arg Val Thr Ile Ser Cys Arg Ala
             35                  40                  45
Ser Gln Asp Ile Ser Lys Tyr Leu Asn Trp Tyr Gln Gln Lys Pro Asp
 50                  55                  60
Gly Thr Val Lys Leu Leu Ile Tyr His Thr Ser Arg Leu His Ser Gly
 65                  70                  75                  80
Val Pro Ser Arg Phe Ser Gly Ser Gly Ser Gly Thr Asp Tyr Ser Leu
                 85                  90                  95
Thr Ile Ser Asn Leu Glu Gln Glu Asp Ile Ala Thr Tyr Phe Cys Gln
                100                 105                 110
Gln Gly Asn Thr Leu Pro Tyr Thr Phe Gly Gly Gly Thr Lys Leu Glu
                115                 120                 125
Leu Lys Arg Gly Gly Gly Gly Ser Gly Gly Gly Gly Ser Gly Gly Gly
            130                 135                 140
Gly Ser Gly Gly Gly Ser Glu Val Gln Leu Gln Gln Ser Gly Pro
145                 150                 155                 160
Gly Leu Val Ala Pro Ser Gln Ser Leu Ser Val Thr Cys Thr Val Ser
                165                 170                 175
Gly Val Ser Leu Pro Asp Tyr Gly Val Ser Trp Ile Arg Gln Pro Pro
                180                 185                 190
Arg Lys Gly Leu Glu Trp Leu Gly Val Ile Trp Gly Ser Glu Thr Thr
            195                 200                 205
Tyr Tyr Asn Ser Ala Leu Lys Ser Arg Leu Thr Ile Ile Lys Asp Asn
            210                 215                 220
Ser Lys Ser Gln Val Phe Leu Lys Met Asn Ser Leu Gln Thr Asp Asp
225                 230                 235                 240
Thr Ala Ile Tyr Tyr Cys Ala Lys His Tyr Tyr Gly Gly Ser Tyr
                245                 250                 255
Ala Met Asp Tyr Trp Gly Gln Gly Thr Thr Val Thr Val Ser Ser Ala
                260                 265                 270
Leu Ser Asn Ser Ile Met Tyr Phe Ser His Phe Val Pro Val Phe Leu
            275                 280                 285
Pro Ala Lys Pro Thr Thr Thr Pro Ala Pro Arg Pro Pro Thr Pro Ala
            290                 295                 300
Pro Thr Ile Ala Ser Gln Pro Leu Ser Leu Arg Pro Glu Ala Ser Arg
305                 310                 315                 320
Pro Ala Ala Gly Gly Ala Val His Thr Arg Gly Leu Asp Pro Lys Leu
                325                 330                 335
Cys Tyr Leu Leu Asp Gly Ile Leu Phe Ile Tyr Gly Val Ile Leu Thr
                340                 345                 350
Ala Leu Phe Leu Arg Val Lys Phe Ser Arg Ser Ala Asp Ala Pro Ala
            355                 360                 365
Tyr Gln Gln Gly Gln Asn Gln Leu Tyr Asn Glu Leu Asn Leu Gly Arg
            370                 375                 380
Arg Glu Glu Tyr Asp Val Leu Asp Lys Arg Gly Arg Asp Pro Glu
385                 390                 395                 400
Met Gly Gly Lys Pro Arg Arg Lys Asn Pro Gln Glu Gly Leu Tyr Asn
                405                 410                 415
Glu Leu Gln Lys Asp Lys Met Ala Glu Ala Tyr Ser Glu Ile Gly Met
            420                 425                 430
Lys Gly Glu Arg Arg Arg Gly Lys Gly His Asp Gly Leu Tyr Gln Gly
            435                 440                 445
```

Leu Ser Thr Ala Thr Lys Asp Thr Tyr Asp Ala Leu His Met Gln Ala
            450                 455                 460

Leu Pro Pro Arg
465

<210> SEQ ID NO 10
<211> LENGTH: 1437
<212> TYPE: DNA
<213> ORGANISM: Artificial Sequence
<220> FEATURE:
<223> OTHER INFORMATION: synthetic CD33-CAR DNA sequence

<400> SEQUENCE: 10

```
cccgggaatt cgccaccatg gactggatct ggcggatcct gttcctcgtg ggagccgcca      60
caggcgccca ttctgcccag cccgccgaca tccagatgac ccagagccct agcagcctga     120
gcgccagcgt gggcgacaga gtgaccatca cctgtcgggc cagcgagagc gtggacaact     180
acggcatcag cttcatgaac tggttccagc agaagcccgg caaggccccc aagctgctga     240
tctacgccgc cagcaatcag ggcagcggcg tgcccagcag attcagcggc tctggcagcg     300
gcaccgactt caccctgacc atcagcagcc tgcagcccga cgacttcgcc acctactact     360
gccagcagag caaagaggtg ccctggacct tcggccaggg caccaaggtg gaaatcaagg     420
gcggaggcgg cagcggaggt ggaggaagtg gcggcggagg atctcaggtg cagctggtgc     480
agtctggcgc cgaagtgaag aaacccggca gcagcgtgaa ggtgtcctgc aaggccagcg     540
gctacacctt caccgactac aacatgcact gggtccgcca ggccccaggc cagggactgg     600
aatggatcgc tacatctac ccctacaacg gcggcaccgg ctacaaccag aagttcaaga     660
gcaaggccac catcaccgcc gacgagagca ccaacaccgc ctacatggaa ctgagcagcc     720
tgcggagcga ggacaccgcc gtgtactact gcgccagagg cagacccgcc atggactact     780
ggggccaggg aaccctggtg acagtgtcca gcgccctgag caacagcatc atgtacttca     840
gccacttcgt gcccgtgttt ctgcccgcca agcccaccac caccccctgcc cctagacctc     900
ccaccccagc cccaacaatc gccagccagc tctgtccct gcggcccgaa gctagcagac     960
ctgctgccgg cggagccgtg cacaccgag gcctggaccc caagctgtgc tacctgctgg    1020
acggcatcct gttcatctac ggcgtgatcc tgaccgccct gttcctgaga gtgaagttca    1080
gcagaagcgc cgacgcccct gcctaccagc agggccagaa ccagctgtac aacgagctga    1140
acctgggcag acgggaagag tacgacgtgc tggacaagcg gagaggcagg gaccccgaga    1200
tgggcggcaa gccagacgg aagaaccccc aggaaggcct gtataacgaa ctgcagaaag    1260
acaagatggc cgaggcctac agcgagatcg gcatgaaggg cgagcggcgg aggggcaagg    1320
gccacgatgg actgtaccag ggcctgagca ccgccaccaa ggacacctac gacgccctgc    1380
acatgcaggc cctgccccc agatgacagc cagggcattt ctccctcgag cggccgc       1437
```

<210> SEQ ID NO 11
<211> LENGTH: 462
<212> TYPE: PRT
<213> ORGANISM: Artificial Sequence
<220> FEATURE:
<223> OTHER INFORMATION: synthetic CD33-CAR amino acid sequence

<400> SEQUENCE: 11

Met Asp Trp Ile Trp Arg Ile Leu Phe Leu Val Gly Ala Ala Thr Gly
1               5                   10                  15

Ala His Ser Ala Gln Pro Ala Asp Ile Gln Met Thr Gln Ser Pro Ser
            20                  25                  30

-continued

```
Ser Leu Ser Ala Ser Val Gly Asp Arg Val Thr Ile Thr Cys Arg Ala
            35                  40                  45

Ser Glu Ser Val Asp Asn Tyr Gly Ile Ser Phe Met Asn Trp Phe Gln
        50                  55                  60

Gln Lys Pro Gly Lys Ala Pro Lys Leu Leu Ile Tyr Ala Ala Ser Asn
65                  70                  75                  80

Gln Gly Ser Gly Val Pro Ser Arg Phe Ser Gly Ser Gly Ser Gly Thr
                85                  90                  95

Asp Phe Thr Leu Thr Ile Ser Ser Leu Gln Pro Asp Asp Phe Ala Thr
            100                 105                 110

Tyr Tyr Cys Gln Gln Ser Lys Glu Val Pro Trp Thr Phe Gly Gln Gly
        115                 120                 125

Thr Lys Val Glu Ile Lys Gly Gly Gly Ser Gly Gly Gly Gly Ser
            130                 135                 140

Gly Gly Gly Gly Ser Gln Val Gln Leu Val Gln Ser Gly Ala Glu Val
145                 150                 155                 160

Lys Lys Pro Gly Ser Ser Val Lys Val Ser Cys Lys Ala Ser Gly Tyr
                165                 170                 175

Thr Phe Thr Asp Tyr Asn Met His Trp Val Arg Gln Ala Pro Gly Gln
            180                 185                 190

Gly Leu Glu Trp Ile Gly Tyr Ile Tyr Pro Tyr Asn Gly Gly Thr Gly
        195                 200                 205

Tyr Asn Gln Lys Phe Lys Ser Lys Ala Thr Ile Thr Ala Asp Glu Ser
    210                 215                 220

Thr Asn Thr Ala Tyr Met Glu Leu Ser Ser Leu Arg Ser Glu Asp Thr
225                 230                 235                 240

Ala Val Tyr Tyr Cys Ala Arg Gly Arg Pro Ala Met Asp Tyr Trp Gly
                245                 250                 255

Gln Gly Thr Leu Val Thr Val Ser Ser Ala Leu Ser Asn Ser Ile Met
            260                 265                 270

Tyr Phe Ser His Phe Val Pro Val Phe Leu Pro Ala Lys Pro Thr Thr
        275                 280                 285

Thr Pro Ala Pro Arg Pro Pro Thr Pro Ala Pro Thr Ile Ala Ser Gln
    290                 295                 300

Pro Leu Ser Leu Arg Pro Glu Ala Ser Arg Pro Ala Ala Gly Gly Ala
305                 310                 315                 320

Val His Thr Arg Gly Leu Asp Pro Lys Leu Cys Tyr Leu Leu Asp Gly
                325                 330                 335

Ile Leu Phe Ile Tyr Gly Val Ile Leu Thr Ala Leu Phe Leu Arg Val
            340                 345                 350

Lys Phe Ser Arg Ser Ala Asp Ala Pro Ala Tyr Gln Gln Gly Gln Asn
        355                 360                 365

Gln Leu Tyr Asn Glu Leu Asn Leu Gly Arg Arg Glu Glu Tyr Asp Val
    370                 375                 380

Leu Asp Lys Arg Arg Gly Arg Asp Pro Glu Met Gly Gly Lys Pro Arg
385                 390                 395                 400

Arg Lys Asn Pro Gln Glu Gly Leu Tyr Asn Glu Leu Gln Lys Asp Lys
                405                 410                 415

Met Ala Glu Ala Tyr Ser Glu Ile Gly Met Lys Gly Glu Arg Arg Arg
            420                 425                 430

Gly Lys Gly His Asp Gly Leu Tyr Gln Gly Leu Ser Thr Ala Thr Lys
        435                 440                 445
```

Asp Thr Tyr Asp Ala Leu His Met Gln Ala Leu Pro Pro Arg
        450                 455                 460

<210> SEQ ID NO 12
<211> LENGTH: 1509
<212> TYPE: DNA
<213> ORGANISM: Artificial Sequence
<220> FEATURE:
<223> OTHER INFORMATION: synthetic CSPG4-CAR DNA sequence

<400> SEQUENCE: 12

```
cccgggaatt cgccaccatg gactggatct ggcgcatcct cttcctcgtc ggcgctgcta      60
ccggcgctca ttcggcccag ccggccgata tcgagctcac ccaatctcca aaattcatgt     120
ccacatcagt aggagacagg gtcagcgtca cctgcaaggc cagtcagaat gtggatacta     180
atgtagcgtg gtatcaacaa aaaccagggc aatctcctga accactgctt ttctcggcat     240
cctaccgtta cactggagtc cctgatcgct tcacaggcag tggatctggg acagatttca     300
ctctcaccat cagcaatgtg cagtctgaag acttggcaga gtatttctgt cagcaatata     360
acagctatcc tctgacgttc ggtggcggca ccaagctgga aatcaaacgg ctgccgcag      420
aaggtggagg cggttcaggt ggcggaggtt ccggcggagg tggctctggc ggtggcggat     480
cggccatggc ccaggtgaag ctgcagcagt caggaggggg cttggtgcaa cctggaggat     540
ccatgaaact ctcctgtgtt gtctctggat tcactttcag taattactgg atgaactggg     600
tccgccagtc tccagagaag gggcttgagt ggattgcaga aattagattg aaatccaata     660
attttggaag atattatgcg gagtctgtga aagggaggtt caccatctca agagatgatt     720
ccaaaagtag tgcctacctg caaatgatca acctaagagc tgaagatact ggcatttatt     780
actgtaccag ttatggtaac tacgttgggc actattttga ccactggggc caagggacca     840
cggtcaccgt atcgagtgcc gcggttctag agctcttgag caactccatc atgtacttca     900
gccacttcgt gccggtcttc ctgccagcga agcccaccac gacgccagcg ccgcgaccac     960
caacaccggc gcccaccatc gcgtcgcagc ccctgtccct gcgcccagag gcgtgccggc    1020
cagcggcggg gggcgcagtg cacacgaggg ggctggacct gctggatccc aaactctgct    1080
acctgctgga tggaatcctc ttcatctatg gtgtcattct cactgccttg ttcctgagag    1140
tgaagttcag caggagcgca gacgcccccg cgtaccagca gggccagaac cagctctata    1200
acgagctcaa tctaggacga gagaggagta cgatgttttt ggacaagaga cgtggccggg    1260
accctgagat gggggggaaag ccgcagagaa ggaagaaccc tcaggaaggc ctgtacaatg    1320
aactgcagaa agataagatg gcggaggcct acagtgagat tgggatgaaa ggcgagcgcc    1380
ggaggggcaa ggggcacgat ggcctttacc agggtctcag tacagccacc aaggacacct    1440
acgacgccct tcacatgcag gccctgcccc ctcgctaaca gccagggcat ttctccctcg    1500
agcggccgc                                                            1509
```

<210> SEQ ID NO 13
<211> LENGTH: 486
<212> TYPE: PRT
<213> ORGANISM: Artificial Sequence
<220> FEATURE:
<223> OTHER INFORMATION: synthetic CSPG4-CAR amino acid sequence

<400> SEQUENCE: 13

Met Asp Trp Ile Trp Arg Ile Leu Phe Leu Val Gly Ala Ala Thr Gly
1               5                   10                  15

Ala His Ser Ala Gln Pro Ala Asp Ile Glu Leu Thr Gln Ser Pro Lys

```
                20                  25                  30
Phe Met Ser Thr Ser Val Gly Asp Arg Val Ser Val Thr Cys Lys Ala
            35                  40                  45
Ser Gln Asn Val Asp Thr Asn Val Ala Trp Tyr Gln Gln Lys Pro Gly
50                  55                  60
Gln Ser Pro Glu Pro Leu Leu Phe Ser Ala Ser Tyr Arg Tyr Thr Gly
65                  70                  75                  80
Val Pro Asp Arg Phe Thr Gly Ser Gly Ser Gly Thr Asp Phe Thr Leu
                85                  90                  95
Thr Ile Ser Asn Val Gln Ser Glu Asp Leu Ala Glu Tyr Phe Cys Gln
            100                 105                 110
Gln Tyr Asn Ser Tyr Pro Leu Thr Phe Gly Gly Gly Thr Lys Leu Glu
            115                 120                 125
Ile Lys Arg Ala Ala Glu Gly Gly Gly Ser Gly Gly Gly Gly
            130                 135                 140
Ser Gly Gly Gly Ser Gly Gly Gly Gly Ser Ala Met Ala Gln Val
145                 150                 155                 160
Lys Leu Gln Gln Ser Gly Gly Gly Leu Val Gln Pro Gly Gly Ser Met
                165                 170                 175
Lys Leu Ser Cys Val Val Ser Gly Phe Thr Phe Ser Asn Tyr Trp Met
            180                 185                 190
Asn Trp Val Arg Gln Ser Pro Glu Lys Gly Leu Glu Trp Ile Ala Glu
            195                 200                 205
Ile Arg Leu Lys Ser Asn Asn Phe Gly Arg Tyr Tyr Ala Glu Ser Val
            210                 215                 220
Lys Gly Arg Phe Thr Ile Ser Arg Asp Asp Ser Lys Ser Ser Ala Tyr
225                 230                 235                 240
Leu Gln Met Ile Asn Leu Arg Ala Glu Asp Thr Gly Ile Tyr Tyr Cys
                245                 250                 255
Thr Ser Tyr Gly Asn Tyr Val Gly His Tyr Phe Asp His Trp Gly Gln
            260                 265                 270
Gly Thr Thr Val Thr Val Ser Ser Ala Ala Val Leu Glu Leu Leu Ser
            275                 280                 285
Asn Ser Ile Met Tyr Phe Ser His Phe Val Pro Val Phe Leu Pro Ala
            290                 295                 300
Lys Pro Thr Thr Thr Pro Ala Pro Arg Pro Pro Thr Pro Ala Pro Thr
305                 310                 315                 320
Ile Ala Ser Gln Pro Leu Ser Leu Arg Pro Glu Ala Cys Arg Pro Ala
                325                 330                 335
Ala Gly Gly Ala Val His Thr Arg Gly Leu Asp Leu Leu Asp Pro Lys
            340                 345                 350
Leu Cys Tyr Leu Leu Asp Gly Ile Leu Phe Ile Tyr Gly Val Ile Leu
            355                 360                 365
Thr Ala Leu Phe Leu Arg Val Lys Phe Ser Arg Ser Ala Asp Ala Pro
            370                 375                 380
Ala Tyr Gln Gln Gly Gln Asn Gln Leu Tyr Asn Glu Leu Asn Leu Gly
385                 390                 395                 400
Arg Arg Glu Glu Tyr Asp Val Leu Asp Lys Arg Gly Arg Asp Pro
                405                 410                 415
Glu Met Gly Gly Lys Pro Gln Arg Arg Lys Asn Pro Gln Glu Gly Leu
            420                 425                 430
Tyr Asn Glu Leu Gln Lys Asp Lys Met Ala Glu Ala Tyr Ser Glu Ile
            435                 440                 445
```

```
Gly Met Lys Gly Glu Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485
```